US009155290B2

(12) United States Patent
Rojas et al.

(10) Patent No.: US 9,155,290 B2
(45) Date of Patent: Oct. 13, 2015

(54) HUMANIZED IL-15 ANIMALS

(71) Applicant: Regeneron Pharmaceuticals, Inc., Tarrytown, NY (US)

(72) Inventors: Jose F. Rojas, Newburgh, NY (US); Ka-Man Venus Lai, Tarrytown, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 14/514,454

(22) Filed: Oct. 15, 2014

(65) Prior Publication Data

US 2015/0106961 A1   Apr. 16, 2015

Related U.S. Application Data

(60) Provisional application No. 61/891,013, filed on Oct. 15, 2013.

(51) Int. Cl.
*A01K 67/027* (2006.01)
*C12N 15/85* (2006.01)
*C07K 14/54* (2006.01)

(52) U.S. Cl.
CPC ......... *A01K 67/0278* (2013.01); *C07K 14/5443* (2013.01); *C12N 15/8509* (2013.01); *A01K 2207/15* (2013.01); *A01K 2217/07* (2013.01); *A01K 2217/072* (2013.01); *A01K 2227/105* (2013.01); *A01K 2267/03* (2013.01); *A01K 2267/0387* (2013.01); *C12N 2015/8527* (2013.01)

(58) Field of Classification Search
CPC ............... A01K 2217/05; A01K 2227/105; A01K 2267/0331; A01K 67/0275; A01K 2217/077; A01K 2267/0387; A01K 2039/55527; A01K 49/0008; C07K 14/5443; C07K 14/7155; C07K 16/244; C12N 15/8509; C12N 2501/231
See application file for complete search history.

(56) References Cited

U.S. PATENT DOCUMENTS 7,759,541 B2 * 7/2010 Wolf et al. ............... 800/18

FOREIGN PATENT DOCUMENTS

| WO | 01/58914 A2 | 8/2001 |
| WO | WO/2012/112544 * | 8/2012 |
| WO | 2013/063556 A1 | 5/2013 |

OTHER PUBLICATIONS

Clark et al. (2003) Nature Reviews: Genetics. vol. 4, 825-833.*
Niemann et al (2005) Rev. Sci, Tech. Off. Int. Spiz. vol. (24), 285-298.*
Wheeler Theriogenology. 2001, 56, 1345-1369.*
Munoz et al. (2009) Stem Cell Rev. And Rep., vol. 5, 6-9.*
Fehniger et al Blood, 2001, 87, 14-32.*
Marks-Konczalik, et al (Proc. Natl. Acad. Sci. USA, 2000, 97, 11445-11450.*
Willinger et al (Trends in Immunology Jul. 2011, vol. 32, No. 7, 321-327.*
Van Der Weyden et al, Physiological Genomics, 2002. 11:133-164.*
Marks-Konczalik, J. et al., "IL-2-induced activation-induced cell death is inhibited in IL-15 transgenic mice" PNAS (Oct. 10, 2000) pp. 11445-11450, vol. 97, No. 21.
Fehniger, T. et al., "Fatal Leukemia in Interkeukin-15 Transgenic Mice" Blood Cells, Molecules and Diseases (Jan./Feb. 2001) pp. 223-230, vol. 27, No. 1.
Fehniger, T. et al., "Interleukin 15: biology and relevance to human disease" Blood (Jan. 2001) pp. 14-32, vol. 97, No. 1.
Devoy, A. et al., "Genomically humanized mice: technologies and promises" Nature Reviews Genetics (Jan. 2012) pp. 14-20, vol. 13.
International Search Report and Written Opinion dated Jan. 26, 2015 issued in International Application No. PCT/US2014/060568.
Anderson, P., "Post-transcriptional control of cytokine production" Nature Immunology (Apr. 2008) pp. 353-359, vol. 9, No. 4.
Carpenter, S. et al., "Post-transcriptional regulation of gene expression in innate immunity" Nature Reviews, Immunology (Jun. 2014) pp. 361-376, vol. 14.
Rongvaux, A. et al., "Human thrombopoietin knockin mice efficiently support human hematopoiesis in vivo" PNAS (Feb. 2011) pp. 2378-2383, vol. 108, No. 6.
Willinger, T. et al., "Human IL-3/GM-CSF knock-in mice support human alveolar macrophage development and human immune responses in the lung" PNAS (2011) pp. 2390-2395, vol. 108, No. 6.
Bamford, R.N. et al., "The 5' Untranslated Region, Signal Peptide, and the Coding Sequence of the Carboxyl Terminus of IL-15 Participate in Its Multifaceted Translational Control" The Journal of Immunology (1998) pp. 4418-4426, vol. 160.
Budagian, V. et al., "IL-15/IL-15 receptor biology: A guided tour through an expanding universe" *Cytokine & Growth Factor Reviews* (2006) pp. 259-280, vol. 17.
Burton, J.D. et al., "A lymphokine, provisionally designated interleukin T and produced by a human adult T-cell leukemia line, stimulates T-cell proliferation and the induction of lymphokine-activated killer cells" *Proc. Natl. Acad. Sci. USA* (1994) pp. 4935-4939, vol. 91.
Fehninger T.A. et al., "Interleukin 15: biology and relevance to human disease" *Blood* (2001) pp. 14-32, vol. 97, No. 1.
Ferrari-Lacraz, S. et al., "Targeting IL-15 Receptor-Bearing Cells with an Antagonist Mutant IL-15/Fc Protein Prevents Disease Development and Progression in Murine Collagen-Induced Arthritis" *J. Immunol.* (2004) pp. 5815-5826, vol. 173.

(Continued)

*Primary Examiner* — Anoop Singh
(74) *Attorney, Agent, or Firm* — Scully, Scott, Murphy & Presser, P.C.; Neil Miyamoto

(57) ABSTRACT

Genetically modified non-human animals comprising a humanized interleukin-15 (IL-15) gene. Cells, embryos, and non-human animals comprising a human IL-15 gene. Rodents that express humanized or human IL-15 protein.

4 Claims, 10 Drawing Sheets

(56) References Cited

OTHER PUBLICATIONS

Grabstein, K.H. et al., "Cloning of a T Cell Growth Factor That Interacts with the β Chain of the Interleukin-2 Receptor" *Science* (1994) pp. 965-968, vol. 264.

Lodolce, J.P. "Regulation of lymphoid homeostasis by interleukin-15" *Cytokine & Growth Factor Reviews* (2002) pp. 429-439, vol. 13.

McInnes, I.B. et al., "Interleukin-15: a new cytokine target for the treatment of inflammatory diseases" *Current Opinion in Pharmacology* (2004) pp. 392-397, vol. 4.

McInnes, I.B. et al., "Interleukin-15 mediates T cell-dependent regulation of tumor necrosis factor-α production in rheumatoid arthritis" *Nature Med.* (1997) pp. 189-195, vol. 3.

Nishimura, H. et al., "A novel autoregulatory mechanism for transcriptional activation of the IL-15 gene by nonsecretable isoform of IL-15 generated by alternative splicing" *FASEB J.* (2005) pp. 19-28, vol. 19.

Ohta, N. et al., "IL-15-dependent activation-induced cell death-resistant Th1 type CD8 alpha beta + NK1.1+ T cells for the development of small intestinal inflammation" *J. Immunol.* (2002) pp. 460-468, vol. 169.

Oppenheimer-Marks, N., "Interleukin 15 is Produced by Endothelial Cells and Increases the Transendothelial Migration of T Cells in Vitro and in the SCID Mouse-Human Rheumatoid Arthritis Model In Vitro" *J. Clin. Invest.* (1998) pp. 1261-1272, vol. 101, No. 6.

Quinn, L.S. et al., "Oversecretion of interleukin-15 from skeletal muscle reduces adiposity" *Am. J. Physiol. Endocrinol. Metab.* (2002) pp. E191-E202, vol. 296.

Quinn, L.S. et al., "Overexpression of interleukin-15 in mice promotes resistance to diet-induced obesity, increased insulin sensitivity, and markers of oxidative skeletal muscle metabolism" *International Journal of Interferon, Cytokine and Mediator Research* (2011) pp. 29-42, vol. 3.

Ruchatz, H. et al., "Soluble IL-15 receptor α-chain administration prevents murine collagen-induced arthritis: a role for IL-15 in development of antigen-induced immunopathology" *J. Immunol.* (1998) pp. 5654-5660, vol. 160.

Steel, J.C. et al., "Interleukin-15 biology and its therapeutic implications in cancer" *Trends in Pharmacological Sciences* (2012) pp. 35-41, vol. 33, No. 1.

Villadsen, L.S. "Resolution of psoriasis upon blockade of IL-15 biological activity in a xenograft mouse model" *J. Clin. Invest.* (2003) pp. 1571-1580, vol. 112, No. 10.

Waldmann, T.A., "The biology of interleukin-2 and interleukin-15: implications for cancer therapy and vaccine design" *Nature Rev. Immunol.* (2006) pp. 595-601, vol. 6.

Yajima, T., "Overexpression of Interleukin-15 Increases Susceptibility to Lipopolysaccharide-Induced Liver Injury in Mice Primed with *Mycobacterium bovis* Bacillus Calmette-Guérin" *Infection and Immunity* (2004) pp. 3855-3862, vol. 72, No. 7.

Yajima, T. et al., "Memory phenotype CD8(+) T cells in IL-15 transgenic mice are involved in early protection against a primary infection with *Listeria monocytogenes*" *Eur.J. Immunol.* (2001) pp. 757-766, vol. 31, No. 3.

Yokoyama, S. et al., "Antibody-mediated blockade of IL-15 reverses the autoimmune intestinal damage in transgenic mice that overexpress IL-15 in enterocytes" *Proc. Natl. Acad. Sci. USA* (2008) pp. 15849-15854, vol. 106, No. 3; and.

Yokoyama, S. et al., "Transgenic Mice that Overexpress Human IL-15 in Enterocytes Recapitualte Both B and T Cell-Mediated Pathologic Manifestations of Celiac Disease" *J. Clin. Immunol.* (2011) pp. 1038-1044, vol. 31.

\* cited by examiner

....ATCCATTTAGCCCTTTCTCTGATCACTAAGTTGGACAGTTGGACA
GTCTTCCTCAAATTAGCTTAGACTATCAAAATTATACTGTATTTTTG
GTATTCCAgcgatcgcTTCAGTTACAAGGCTGTTGAATGCACAGAA
GCAAGGATAACACTGATTTTTCACTGGTCAGAATAAAAATTATTGA
TTGCTCTTTTGCTTATAGTATTC......(SEQ ID NO:1)

FIG. 2

..........AATGTAACAGAATCTGGATGCAAAGAATGTGAGGAACTGGAGGAAAAATATTAAAGAATTTTGCAG
AGTTTTGTACATATTGTCCAAATGTTCATCAACACTTCTTGATTGCAATTGATTCTTTTAAAGTGTTTCTGTTATTAA
CAAACATCACTCTGCTGCTTAGACATAACAAACACTCGGCATTTCAAATGTGCTGTCAAAACAAGTTTTCTGTCAAG
AAGATGATCAGACCTTGGATCAGATGAACTCTTAGAAATGAAGGCAGAAAAATGTCATTGAGTAATATAGTGACTATGA
ACTTCTCTCAGACTTACTTACTCATTTTTTAATTATTATTGAAATTGTACATATTTGTGGAATAATGTAAAATGTT
GAATAAAAATATGTACAAGTGTGTTTTTTAAGTTGCACTGACCAAATTTACCTCTCTTATTGCAAAATAGCATTTGTTAAG
GGTGATAGTCAAATTATGTATTGGTGGGGCTGGTACCAAATGCTGCAGGTCAACACTATGCTGGTAGGCTCCTGCCAG
TGTGGAACCACTGACTACTGGCTCTCATTGACTCCTTACTGTAATTTAGTTATTGATGTATAAAGCAACTGTTATCAGTAAG
AAAAAGAAGAACTATATGTGAATCGCATATAATGTCCATCAGTAAATCTTGGTGGTGGCAATAATAAACTTCTACTGATAGG
TAGAATGGTGTGCAAGCTTGTCCAATCACGGATTGCAGGCCACATGCGGCCACAGCCAAATCTTGAATGTGGCCCAAG
AAATTCATAAAACTTTCATACACATCTCGTTTTTAGCTCATCAGCTATCATTAGCGGTAGTGTATTTAAAGTGTGGCCAAG
ACAATTCTTCTTATTCCAATGTGGCCCAGGAAATCAAAAGATTGGATGCCCCTGGTATAGAAAACTAATAGTGACAGT
GTTCATATTTCATGCTTTCCCAAATACAGTTGTTATCTGACAGAAAATAATTGTTTATATTTTTTGCACTACACTGTCTAAAAT
AACCCTGTTGATTTGTTGGAGCCATTGTAACTGATGAAGATGTAAGAATGATGAAATATTTTGTTTTATTATATAAATTTATTTCACCTTAATTCT
TAGCAAGCTCTCTCTTCTAATGGAACTGAGTGACTGTGGGGGTGGAAATGATCTCTTAAGAATTTGATTTCTTTCTATTCCATAGTACAAACT
CGTTCTCTGTTGAAACATTCTTCTATCACCCCAGTGCCTATCCATGTACACATGTGTTCTTATTGCTCTAGTCAAACGGT
GCTTATAAATATCTTTCAGAAAGTTTAGGAGAAATCTGTATCCTATTGACTTCCAATAATCATGTATTGGCTGTCAGC
TTCTTACCTACTCTCCAGTCCAGAGAAATAGTATTTGGCAGCCACTCTCTTTAAAGTTTATGGGTGTGTTTTATGTAGCTTTCTA
GATTTATTTTTTATTCAATTGGGATAGAATTTTTAATATACCTGTATTTTTGTTTTTTGGAATGTTAGTCTTCCTGA
TTAGGGAGAGTAGGAAAAGTGCACCATTTCTTCTCTCTAAATTTCCAGTCCAGTCTTTAGGGAATGTTAGTCTTCCTGA
GATGGGGAAGGAAAATCATAAATGCCAGTCACTTTGCAAATAATATTTTATAGTGATAAATGGTTCATTTTGGTTACAT
AGGCATACAAGTGGGCTTAAGAACTTGGAATTTACCAGGGCATAGATCTGCAACctcgagATAACTTCGTATAATGTATACGAAG
CGCTTCAGTTGATCTTGAAGCTCAAGGCATAGATCTGCAACctcgagATAACTTCGTATAATGTATGCTATACGAAG
TTATATGCATGCCTCCGCGCCGGGGGTTTTGGCGCTCCGCGGGGCCCCTCCCTCACGGCGA (SEQ ID
NO:2)........2.6Kb

FIG. 3

2.6Kb...CATTCTCAGTATTGTTTTGCCAAGTTCTAATTCCATCAGACC
TCGACCTGCAGCCCCTAGATAAACTTCGTATAATGTATGCTATACGAAGT
TATgctagcGTGATAGTCCTTCACGGAAAGTACAAGAATACACAGAAAA
CTGCTGTTTACATTAGTCTTTCACGTTTTTATTTTATTCTCACAAATTT
TAATGCAATAC... (SEQ ID NO:3)

FIG. 4

```
mIl15_precursor      1 MKILKPYMRNTSISCYLCFLLNSHFLTEAG  30
Regn_Hybrid_m/h      1 MKILKPYMRNTSISCYLCFLLNSHFLTEAG  30
hIL15 isoform 1      1 MRISKPHLRSISIQCYLCLLLNSHFLTEAG  30 mIl15_precursor     31 IHVFILGCVSVGLPKTEANWIDVRYDLEKI  60
Regn_Hybrid_m/h     31 IHVFILGCFSAGLPKTEANWVNVISDLKKI  60
hIL15 isoform 1     31 IHVFILGCFSAGLPKTEANWVNVISDLKKI  60 mIl15_precursor     61 ESLIQSIHIDTTLYTDSDFHPSCKVTAMNC  90
Regn_Hybrid_m/h     61 EDLIQSMHIDATLYTESDVHPSCKVTAMKC  90
hIL15 isoform 1     61 EDLIQSMHIDATLYTESDVHPSCKVTAMKC  90 mIl15_precursor     91 FLLELQVILHEYSNMTLNETVRNVLYLANS 120
Regn_Hybrid_m/h     91 FLLELQVISLESGDASIHDTVENLIIILANN 120
hIL15 isoform 1     91 FLLELQVISLESGDASIHDTVENLIIILANN 120 mIl15_precursor    121 TLSSNKNVAESGCKECEELEEKTFTEFLQS 150
Regn_Hybrid_m/h    121 SLSSNGNVTESGCKECEELEEKNIKEFLQS 150
hIL15 isoform 1    121 SLSSNGNVTESGCKECEELEEKNIKEFLQS 150 mIl15_precursor    151 FIRIVQMFINTS 162 (SEQ ID NO:4)
Regn_Hybrid_m/h    151 FVHIVQMFINTS 162 (SEQ ID NO:5)
hIL15 isoform 1    151 FVHIVQMFINTS 162 (SEQ ID NO:6)
```

HUMANIZED IL-15 ANIMALS

FIELD

Non-human animals comprising in their germline a humanized endogenous non-human IL-15 locus. Non-human animals comprising in their germline a humanized IL-15-encoding sequence under control of endogenous non-human regulatory elements. Non-human animals (e.g., mammals, e.g., rodents such as mice, rats, and hamsters) that comprise a genetic modification comprising a replacement, at an endogenous locus, of a non-human IL-15 gene sequence with a human or humanized IL-15 gene sequence. Rodents and other non-human animals that express human or humanized IL-15 from an endogenous modified non-human IL-15 locus. Non-human animals that express human or humanized IL-15 under the control of a non-human IL-15 promoter and/or regulatory sequences.

INCORPORATION BY REFERENCE OF SEQUENCE LISTING

The Sequence Listing in the ASCII text file, named as 31013_SEQ.txt of 9 KB, created on Oct. 14, 2014, and submitted to the United States Patent and Trademark Office via EFS-Web, is incorporated herein by reference.

BACKGROUND

Transgenic mice with randomly inserted transgenes that contain a human IL-15 sequence are known in the art. However, transgenic mice that express human IL-15 from randomly integrated transgenes are not optimal in one respect or another. For example, most mice transgenic for human IL-15 exhibit abnormal levels and/or ratios of certain cells, including lymphocytes (e.g., T cells), that are likely due to a dysregulation of immune cell function. Such mice also exhibit a panoply of pathologies, presumably ultimately due to dysregulation of the transgenic IL-15. Such dysregulation may result from, e.g., absence of endogenous control elements, and/or placement of the human IL-15 sequence away from the endogenous IL-15 locus.

There remains a need in the art for non-human animals that comprise human IL-15-encoding sequences, wherein the human IL-15 encoding sequences are at an endogenous non-human IL-15 locus, and/or are under regulatory control of endogenous non-human IL-15 elements (e.g., upstream and/or downstream noncoding regions). There is a need in the art for non-human animals that express human IL-15 under the control of endogenous non-human regulatory elements. There is a need in the art for non-human animals that express human IL-15 in a manner that is physiologically relevant in the non-human animal. There is a need in the art for non-human animals that express a human IL-15, wherein the non-human animals lack a significant abnormality in lymphocyte populations, e.g., in T cell populations. There is also a need in the art for non-human animals that express human or humanized IL-15, and that lack one or more of the pathologies exhibited by non-human animals that are transgenic for human IL-15.

SUMMARY

In various aspects and embodiments, genetically modified non-human organisms comprising a humanized IL-15 locus are provided. Non-human organisms that comprise a humanized IL-15 gene are provided, wherein the humanized IL-15 gene is under control of one or more endogenous non-human regulatory elements. Non-human organisms that comprise a humanized IL-15 gene at an endogenous non-human IL-15 locus are provided. Non-human organisms that comprise an endogenous humanized IL-15 locus that is capable of being passed through the germline of the organisms are provided. Non-human animals, e.g., mammals (e.g., rodents, e.g., mice or rats) that express human IL-15 from a modified endogenous IL-15 locus are provided, wherein the expressed IL-15 is fully or partly human.

Genetically modified non-human animals, embryos, cells, tissues, and nucleic acids are provided, which comprise a human IL-15 genomic sequence regulated by non-human IL-15 regulatory control. The non-human animals express a humanized IL-15 protein, or fully human IL-15 protein (e.g., a fully human mature IL-15 protein), and do not exhibit one or more of the pathologies of transgenic human IL-15 non-human animals known in the art. In various embodiments, the non-human animals are mammals, e.g., rodents, e.g., mice, rats, hamsters, etc. In a specific embodiment, the mammal is a rodent; in another specific embodiment, the rodent is a mouse or a rat.

Genetically modified non-human animals, embryos, cells, tissues, and nucleic acids are provided, which comprise a human IL-15 genomic sequence at an endogenous non-human IL-15 locus. The non-human animals express a humanized IL-15 protein, or fully human IL-15 protein (e.g., a fully human mature IL-15 protein), from a modified endogenous non-human locus regulated by one or more endogenous non-human regulatory sequences of the modified endogenous IL-15 locus, and do not exhibit one or more of the pathologies of transgenic human IL-15 non-human animals known in the art. In various embodiments, the non-human animals are mammals, e.g., rodents, e.g., mice, rats, hamsters, etc. In a specific embodiment, the mammal is a rodent; in another specific embodiment, the rodent is a mouse or a rat.

In various embodiments and aspects, the non-human animals comprise a modified IL-15 locus in the genome of the non-human animal such that the modified IL-15 locus is capable of being passed through the germline, wherein the modified endogenous IL-15 locus comprises a humanization of at least a mature protein-coding portion of the endogenous IL-15 locus. In various embodiments, the non-human animals are mammals. In various embodiments, the mammals are rodents, and the rodents are heterozygous or homozygous with respect to the modified IL-15 locus. In various embodiments, the rodents are selected from mice and rats. In various embodiments, the mice and rats are homozygous for the modified IL-15 locus, and are incapable of expressing an endogenous fully mouse or fully rat IL-15 protein, and the mice and rats express a mature human IL-15 protein.

In one embodiment, a non-human animal is provided that comprises a first endogenous wild-type IL-15 allele, and a humanization of a second endogenous IL-15 allele.

In one embodiment, a non-human animal is provided that comprises a lack of a first endogenous IL-15 allele and a humanization of a second endogenous IL-15 allele.

In one embodiment, a non-human animal is provided that comprises a lack of a functional endogenous IL-15 allele, and comprise at least one copy of a humanized IL-15 allele under the control of endogenous non-human regulatory elements. In one embodiment, the at least one copy of a humanized IL-15 allele is at an endogenous IL-15 locus.

In various embodiments and aspects, the humanization is of one or more exons and/or introns at the endogenous non-human IL-15 locus. In various embodiments and aspects, non-human animals having a modified IL-15 locus are provided wherein one or both of an endogenous non-human 5'-untranslated region and an endogenous non-human 3'-untranslated region are retained in the modified non-human animal.

In one embodiment, the humanization of the endogenous non-human IL-15 locus is with a coding region (or fragment thereof) that is a genomic fragment of a human IL-15 locus that comprises at least one human IL-15 protein-coding exon.

In one embodiment, the humanization of the endogenous non-human IL-15 locus is with a coding region that is a genomic fragment of a human IL-15 locus that comprises each human IL-15 protein-coding exon, but does not comprise a non-human IL-15 protein-coding exon.

In one embodiment, the IL-15 locus that comprises the human genomic fragment results in the expression of an IL-15 protein that when mature is fully human. In one embodiment, the humanization of the endogenous non-human IL-15 locus is with a cDNA encoding a human IL-15 protein, such that upon processing in the non-human animal the mature IL-15 protein produced by the humanized locus is fully human.

In one aspect, a genetically modified non-human animal is provided that comprises an endogenous IL-15 locus that is humanized in whole or in part, wherein the humanized IL-15 locus comprises a humanized IL-15-coding gene that is under control of endogenous non-human regulatory elements. In one embodiment, the endogenous non-human regulatory elements comprise all endogenous IL-15 regulatory elements upstream (with respect to transcriptional direction of the IL-15 gene) of the first protein-coding region or exon of the humanized IL-15 gene. In one embodiment, the endogenous non-human regulatory elements comprise all endogenous IL-15 regulatory elements downstream (with respect to transcriptional direction of the IL-15 gene) of the last protein-coding region or exon on the humanized IL-15 gene. In one embodiment, the humanized IL-15-coding gene comprises a human 3'UTR.

In one aspect, a genetically modified rodent is provided that comprises a replacement at an endogenous rodent IL-15 locus of an endogenous rodent IL-15 genomic sequence with a human IL-15 genomic sequence. In one embodiment, the genetic modification is in the germline of the non-human animal.

In one embodiment, the genetically modified rodent comprises a first rodent regulatory sequence upstream (with respect to the direction of transcription of the IL-15 gene) of the human IL-15 genomic sequence and a second rodent regulatory sequence downstream of the human IL-15 genomic sequence. In one embodiment, the first rodent regulatory sequence comprises a rodent promoter and/or enhancer, and the second rodent regulatory sequence comprises a 3'-UTR.

In one aspect, a genetically modified non-human animal is provided that expresses a human or humanized IL-15 protein In one aspect, a genetically modified mouse is provided that comprises a replacement at an endogenous mouse IL-15 locus of an endogenous mouse IL-15 genomic sequence (or fragment thereof) with a human IL-15 genomic sequence (or fragment thereof) to form a modified locus, wherein the human IL-15 genomic sequence comprises at least one human protein-coding exon.

In one embodiment, the replacement comprises a human genomic fragment comprising at least two protein-coding exons of human IL-15. In one embodiment, the replacement comprises a human genomic fragment that comprises at least three protein-coding exons of human IL-15. In one embodiment, the replacement comprises a human genomic fragment that comprises at least four protein-coding exons of human IL-15. In one embodiment, the replacement comprises a human genomic fragment that comprises protein-coding exons 3, 4, 5 and 6 of human IL-15. In one embodiment, the replacement comprises less than all human IL-15 exons, wherein the human exons of the replacement consist of the downstream-most (with respect to direction of transcription of the IL-15 gene) four protein-coding exons of the human IL-15 gene. In one embodiment, the replacement consists essentially of a human genomic fragment that contains no more than four protein-coding exons of human IL-15; in one embodiment, the replacement further consists essentially of human intronic sequence upstream of the 5'-most human exon and human non-protein-coding sequence downstream of the human stop codon and downstream of the human 3'UTR.

In one aspect, a genetically modified mouse is provided that comprises a humanized IL-15 locus, wherein the humanized IL-15 locus comprises non-protein-coding mouse exons, wherein each (mature) protein-coding mouse exon is replaced with (mature) protein-coding human exons. In one embodiment, the humanized IL-15 locus comprises a replacement of a mouse genomic fragment that encodes mature (i.e., non pre-protein) mouse IL-15 protein sequences with a human genomic fragment that encodes mature (i.e., non-preprotein) human IL-15 protein sequences.

In one aspect, a genetically modified mouse is provided that comprises a sequence that is at least 95%, 96%, 97%, 98%, or 99% identical, or is identical, to SEQ ID NO:5.

In one aspect, a genetically modified mouse is provided that comprises a sequence that is at least 95%, 96%, 97%, 98%, or 99% identical, or is identical, to SEQ ID NO:5; wherein the mouse lacks an endogenous sequence encoding exons 3 through 6 of a mouse IL-15 protein as depicted herein, and the mouse comprises a nucleic acid sequence at an endogenous mouse IL-15 locus wherein the nucleic acid sequence encodes human IL-15 exons 3, 4, 5, and 6 as depicted herein.

In one aspect, a genetically modified rodent is provided that expresses a human or humanized IL-15 protein from an endogenous mouse IL-15 locus that is modified to comprise at least one human IL-15 exon that encodes amino acids in a mature human IL-15 protein. In one embodiment, the endogenous rodent IL-15 locus comprises at least two human IL-15 exons that encode amino acids in a mature human IL-15 protein. In one embodiment, the endogenous rodent IL-15 locus comprises at least three human IL-15 exons that encode amino acids in a mature human IL-15 protein. In one embodiment, the endogenous rodent IL-15 locus comprises at least four human IL-15 exons that encode amino acids in a mature human IL-15 protein. In one embodiment, the endogenous rodent comprises human IL-15 exons 3, 4, 5 and 6 that encode amino acids in a mature human IL-15 protein. In one embodiment, the endogenous rodent IL-15 locus comprises all human nucleic acid sequence that encodes amino acids in a mature human IL-15 protein.

In one embodiment, the humanization comprises a human IL-15 3'UTR. In one embodiment, the rodent locus comprises at least one exon that does not encode amino acids of a mature IL-15 protein or at least one exon that includes a nucleotide sequence that does not encode amino acids of a mature IL-15 protein. In one embodiment, the rodent locus comprises at least two exons that do not encode amino acids of a mature IL-15 protein. In one embodiment, the rodent locus comprises at least three exons that do not encode amino acids of a mature IL-15 protein. In one embodiment, the rodent locus comprises four exons that do not encode amino acids of a mature IL-15 protein.

In one aspect, a genetically modified rodent is provided that expresses a humanized IL-15 protein, wherein the lymphocyte population of the rodent is characterized by its T cell population that is about the same in number as a population of T cells in an age-matched wild-type mouse. In one embodiment, the modified rodent is characterized by a population of mature T cells that is about the same in number as a population of mature T cells in an age-matched wild-type mouse.

In one aspect, a genetically modified rodent is provided that expresses a humanized IL-15 protein, wherein the lymphocyte population of the rodent is characterized by a population of T cells that is about the same in number as a population of T cells in an age-matched wild-type mouse. In one embodiment, the modified rodent exhibits a population of mature T cells that is about the same in number as a population of mature T cells in an age-matched wild-type mouse. In one embodiment, the modified rodent exhibits a population of peripheral T cells that is about the same in number as the population of peripheral T cells in an age-matched wild-type mouse. In one embodiment, the mature humanized IL-15 protein is identical to a mature human IL-15 protein.

In one aspect, a genetically modified rodent is provided that expresses a humanized IL-15 protein, wherein the lymphocyte population of the rodent is characterized by a T cell population that exhibits a CD4:CD8 ratio that is about the same as the CD4:CD8 ratio in the T cell population of an age-matched wild-type mouse. In one embodiment, the humanized IL-15 protein is identical to a human IL-15 protein.

In one aspect, a genetically modified rodent is provided that expresses a humanized IL-15 protein, wherein the lymphocyte population of the rodent is characterized by a natural killer (NK) cell population that is about the same in size as an NK cell population of an age-matched wild-type mouse. In one embodiment, the humanized IL-15 protein is identical to a human IL-15 protein.

In one aspect, a genetically modified rodent is provided that expresses a human or humanized IL-15 protein, wherein the lymphocyte population of the rodent is characterized by a T cell population and an NK cell population that are each about the same in size as a T cell population and an NK cell population in an age-matched wild-type mouse.

In one aspect, a genetically modified rodent is provided that expresses a humanized IL-15 protein, wherein the rodent does not develop spontaneous intestinal inflammation. In one embodiment, the rodent does not display a propensity to develop intestinal inflammation any more than an age-matched wild-type rodent.

In one aspect, a genetically modified rodent is provided that expresses a humanized IL-15 protein, wherein the rodent does not develop spontaneous inflammation in the duodeno-jejunal area. In one embodiment, the rodent does not display a propensity to develop inflammation in the duodeno-jejunal area any more than an age-matched wild-type rodent.

In one aspect, a genetically modified rodent is provided that expresses a humanized IL-15 protein, wherein the rodent does not exhibit destruction of intestinal epithelium greater than an age-matched wild-type rodent.

In one aspect, a genetically modified rodent is provided that expresses a humanized IL-15 protein, wherein the rodent does not exhibit celiac disease at a higher rate or frequency than an age-matched wild-type rodent.

In one aspect, a genetically modified rodent is provided that expresses a humanized IL-15 protein, wherein the rodent does not exhibit a higher resistance to diet-induced adiposity, and does not exhibit a higher insulin sensitivity, than an age-matched wild-type rodent.

In one aspect, a genetically modified rodent is provided that expresses a humanized IL-15 protein, wherein the rodent upon infection with a pathogen is no more susceptible to lipopolysaccharide-induced lethal liver injury than an age-matched wild-type rodent.

In one aspect, a genetically modified rodent is provided that expresses a humanized IL-15 protein, wherein the rodent does not develop psoriatic lesions at a higher rate or frequency than an age-matched wild-type rodent.

In one aspect, a genetically modified rodent is provided that expresses a humanized IL-15 protein, wherein the rodent does not develop arthritis at a higher rate or frequency than an age-matched wild-type rodent.

In one aspect, a genetically modified rodent is provided that expresses a humanized IL-15 protein, wherein the rodent does not develop lymphocyte infiltration of joints at a higher rate or frequency than an age-matched wild-type rodent.

In one aspect, a genetically modified rodent is provided that expresses a humanized IL-15 protein, wherein the rodent does not develop inflammatory synovitis at a rate higher than an age-matched wild-type control rodent.

In one aspect, a genetically modified rodent is provided that expresses a human or humanized IL-15 protein, wherein the rodent does not develop one or more pathologies at a rate or frequency higher than that of an age-matched wild-type rodent, wherein the one or more pathologies is selected from the group consisting of arthritis, lymphocyte infiltration of joints, inflammatory synovitis, psoriatic lesions, pathogen-related lipopolysaccharide-induced lethal liver injury, a resistance to insulin, a resistance to diet-induced adiposity, spontaneous intestinal inflammation, spontaneous inflammation in the duodeno-jejunal area, destruction of intestinal epithelium, celiac disease, and a combination thereof.

In one aspect, a genetically modified rodent is provided that expresses a human or humanized IL-15 protein, wherein the rodent does not develop two or more pathologies at a rate or frequency higher than that of an age-matched wild-type rodent, wherein the two or more pathologies is selected from the group consisting of arthritis, lymphocyte infiltration of joints, inflammatory synovitis, psoriatic lesions, pathogen-related lipopolysaccharide-induced lethal liver injury, a resistance to insulin, a resistance to diet-induced adiposity, spontaneous intestinal inflammation, spontaneous inflammation in the duodeno-jejunal area, destruction of intestinal epithelium, and celiac disease.

In one aspect, a genetically modified rodent is provided that expresses a human or humanized IL-15 protein, wherein the rodent does not develop three or more pathologies at a rate or frequency higher than that of an age-matched wild-type rodent, wherein the three or more pathologies is selected from the group consisting of arthritis, lymphocyte infiltration of joints, inflammatory synovitis, psoriatic lesions, pathogen-related lipopolysaccharide-induced lethal liver injury, a resistance to insulin, a resistance to diet-induced adiposity, spontaneous intestinal inflammation, spontaneous inflammation in the duodeno-jejunal area, destruction of intestinal epithelium, and celiac disease.

In one aspect, a genetically modified rodent is provided that expresses a human or humanized IL-15 protein, wherein the rodent does not develop four or more pathologies at a rate or frequency higher than that of an age-matched wild-type rodent, wherein the four or more pathologies is selected from the group consisting of arthritis, lymphocyte infiltration of joints, inflammatory synovitis, psoriatic lesions, pathogen-related lipopolysaccharide-induced lethal liver injury, a resistance to insulin, a resistance to diet-induced adiposity, spontaneous intestinal inflammation, spontaneous inflammation in the duodeno-jejunal area, destruction of intestinal epithelium, and celiac disease.

In one aspect, a genetically modified rodent is provided that expresses a human or humanized IL-15 protein, wherein the rodent does not develop five or more pathologies at a rate or frequency higher than that of an age-matched wild-type rodent, wherein the five or more pathologies is selected from the group consisting of arthritis, lymphocyte infiltration of joints, inflammatory synovitis, psoriatic lesions, pathogen-related lipopolysaccharide-induced lethal liver injury, a resistance to insulin, a resistance to diet-induced adiposity, spontaneous intestinal inflammation, spontaneous inflammation in the duodeno-jejunal area, destruction of intestinal epithelium, and celiac disease.

In one aspect, a genetically modified rodent is provided that expresses a human or humanized IL-15 protein, wherein the rodent does not develop six or more pathologies at a rate or frequency higher than that of an age-matched wild-type rodent, wherein the six or more pathologies is selected from the group consisting of arthritis, lymphocyte infiltration of joints, inflammatory synovitis, psoriatic lesions, pathogen-related lipopolysaccharide-induced lethal liver injury, a resistance to insulin, a resistance to diet-induced adiposity, spontaneous intestinal inflammation, spontaneous inflammation in the duodeno-jejunal area, destruction of intestinal epithelium, and celiac disease.

In one aspect, a genetically modified non-human animal is provided that comprises a humanization of an endogenous IL-15 locus, wherein the animal expresses a partly or fully-human mature IL-15 protein, and wherein the partly of fully-human mature IL-15 protein is expressed at comparable levels and in the same tissues as an endogenous IL-15 protein in an age-matched wild-type animal.

In one aspect, a large targeting vector (LTVEC) is provided that comprises homology arms to an endogenous non-human IL-15 locus, wherein the LTVEC comprises, disposed between said homology arms, a contiguous human genomic fragment comprising protein-coding exons of a human IL-15 gene. In one embodiment, the contiguous human genomic fragment does not comprise non-protein-coding exons of a human IL-15 locus. In one embodiment, the contiguous human genomic fragment further comprises a human 3'UTR of an IL-15 gene.

In one aspect, a nucleic acid (e.g., DNA) construct is provided, comprising from 5' to 3' with respect to direction of transcription, a nucleic acid sequence homologous to a mouse IL-15 5' noncoding sequence, a human genomic fragment comprising human IL-15 protein-encoding exons but not comprising a human regulatory sequence upstream with respect to the human IL-15 protein-encoding sequence, and a nucleic acid sequence homologous to a mouse IL-15 3' non-coding sequence. In one embodiment, the human genomic fragment further comprises a human IL-15 3'UTR.

In one aspect, a nucleic acid (e.g., DNA) construct is provided, comprising from 5' to 3' with respect to direction of transcription, a nucleic acid sequence that comprises a region of homology to mouse IL-15 gene sequences upstream of the first mouse IL-15 protein-coding exon, a human genomic fragment encoding a human IL-15 protein but not comprising a human regulatory sequence upstream of sequence encoding the human IL-15 protein, and a nucleic acid sequence homologous to a mouse IL-15 3' noncoding sequence. In one embodiment, the human genomic fragment further comprises a human IL-15 3'UTR.

In one aspect, a genetically modified non-human cell is provided, wherein the non-human cell comprises a replacement at an endogenous non-human IL-15 locus of a gene sequence encoding a non-human IL-15 with a human genomic sequence encoding a human IL-15.

In one embodiment, the human genomic sequence comprises a contiguous human nucleic acid sequence spanning all protein-coding exons of the human IL-15 gene.

In one embodiment, the genetically modified rodent comprises a non-human IL-15 promoter at the endogenous non-human IL-15 locus.

In one embodiment, the genetically modified non-human animal comprises all rodent non-protein-coding exons and regulatory regions upstream of the first protein-coding exon of the rodent IL-15 gene.

In one embodiment, the cell is selected from a pluripotent cell, an induced pluripotent cell, a totipotent cell, an ES cell, a somatic cell, and an ovum.

In one embodiment, the cell expresses human IL-15 protein.

In one embodiment, the non-human animal is a mammal. In one embodiment, the mammal is a rodent. In one embodiment, the rodent is selected from a mouse and a rat.

In one aspect, a non-human embryo is provided, wherein the embryo comprises at least one non-human donor cell (e.g., an ES cell, a pluripotent cell, a totipotent cell, etc.) comprising a replacement of an endogenous non-human IL-15-encoding nucleic acid sequence with a human IL-15-encoding nucleic acid sequence at an endogenous non-human IL-15 locus.

In one embodiment, the donor cell is a non-human ES cell and the embryo is a host non-human animal embryo that is a pre-morula, a morula, or a blastocyst.

In one embodiment, the non-human embryo is a rat embryo, and the at least one non-human donor cell is a rat cell. In one embodiment, the non-human ES cell is a rat ES cell and the host embryo is a rat embryo.

In one embodiment, the non-human embryo is a mouse embryo, and the at least one non-human donor cell is a mouse cell. In one embodiment, the non-human ES cell is a mouse ES cell and the host embryo is a mouse embryo.

In one aspect, a rodent tissue that comprises a humanized IL-15 gene at an endogenous rodent IL-15 locus is provided. In one embodiment, the tissue is selected from epithelial tissue, skin tissue, and muscle tissue.

In one aspect, a genetically modified rodent is provided that comprises a nucleic acid (e.g., DNA) sequence that encodes a human IL-15 protein, wherein the rodent does not express a rodent IL-15, and wherein the rodent exhibits an NK cell population that is about the same size as an NK cell population of a wild-type rodent. In one embodiment, the rodent is a rat. In one embodiment, the rodent is a mouse.

In one embodiment, the rodent exhibits a peripheral T cell population that is about the same size as a peripheral T cell population of an age-matched wild-type rodent.

In one aspect, a method is provided for making a non-human animal that expresses a human or humanized IL-15 protein, comprising genetically modifying a non-human animal as described herein to form a nucleic acid sequence in the non-human animal that comprises a nucleic acid sequence (e.g., DNA) that encodes a human or humanized IL-15 protein, wherein the nucleic acid sequence is under control of endogenous non-human upstream and downstream regulatory elements.

In some embodiments, the non-human animal is genetically modified by replacing an endogenous IL-15 genomic sequence (or fragment thereof), at an endogenous IL-15 locus, with a human IL-15 genomic sequence (or fragment thereof) to form a modified locus, wherein the human IL-15 genomic sequence comprises at least one human protein-coding exon. In one embodiment, the replacement comprises a human genomic fragment comprising at least two protein-coding exons of human IL-15. In one embodiment, the replacement comprises a human genomic fragment that comprises at least three protein-coding exons of human IL-15. In one embodiment, the replacement comprises a human genomic fragment that comprises at least four protein-coding exons of human IL-15. In a specific embodiment, the replacement comprises a human genomic fragment that comprises protein-coding exons 3, 4, 5 and 6 of human IL-15. In one embodiment, the replacement further comprises human non-protein-coding sequence downstream of the human stop codon (e.g., the human 3'UTR).

In one embodiment, the non-human animal is produced from a pluripotent or totipotent cell (e.g., an ES cell). In one embodiment, the non-human animal is produced employing a nuclear injection step wherein a nucleic acid construct comprising the humanized IL-15 gene (optionally with upstream and/or downstream endogenous non-human regulatory sequences) is introduced by pronuclear injection. In one embodiment, the nucleic acid construct comprises a human genomic fragment that comprises protein-coding exons 3, 4, 5 and 6 of human IL-15. In one embodiment, the nucleic acid construct further comprises human non-protein-coding sequence downstream of the human stop codon (e.g., the human 3'UTR). In one embodiment, the non-human animal is produced employing a non-human fibroblast that is genetically modified with a human or humanized IL-15 gene and (optionally) upstream and/or downstream non-human IL-15 regulatory elements.

In one aspect, a method for identifying an agent that is an antagonist of human IL-15 is provided, comprising a step of administering an agent to a genetically modified rodent as described herein, determining an effect of the agent on a human IL-15-mediated function in the rodent, and identifying the agent as an IL-15 antagonist if it antagonizes the function of human IL-15 in the genetically modified rodent.

In one embodiment, the agent comprises an immunoglobulin variable domain that binds IL-15. In one embodiment, the agent specifically binds human IL-15 but not rodent IL-15. In one embodiment, the agent is an antibody.

In one aspect, a method for determining whether an agent reduces IL-15-mediated lymphocyte development is provided, comprising a step of administering to a genetically modified rodent as described herein an IL-15 antagonist for a period of time, measuring a lymphocyte number of the rodent at one or more time points following administration, and determining whether the IL-15 antagonist reduces the lymphocyte population.

In one aspect a method for determining whether an agent reduces IL-15-mediated lymphocyte infiltration of a tissue or a joint is provided, comprising a step of administering to a genetically modified rodent as described herein an IL-15 antagonist for a period of time, measuring lymphocyte infiltration of the tissue or the joint at one or more time points following administration, an determining whether the IL-15 antagonist reduces lymphocyte infiltration of the tissue or joint.

In one aspect, a method is provided for determining whether an agent reduces IL-15-mediated arthritic progression, comprising a step of administering to a genetically modified rodent as described herein, and further comprising an induced arthritis, an IL-15 antagonist for a period of time, measuring arthritic progression, and determining whether the IL-15 antagonist affects arthritic progression in the rodent.

Unless otherwise stated, or apparent from the context, two or more aspects and/or embodiments can be combined.

BRIEF DESCRIPTION OF THE FIGURES

FIG. 2 is a nucleic acid sequence (SEQ ID NO:1) that depicts the upstream (with respect to direction of transcription of the IL-15 gene) junction between mouse sequence and human sequence; the sequence shown begins with mouse sequence in uppercase, followed by an AsisI restriction site in lowercase, followed by human IL-15 nucleic acid sequence in uppercase. The ellipses indicate that sequence continues upstream and downstream of the sequence shown.

FIG. 3 is an embodiment of a nucleic acid sequence (SEQ ID NO:2) indicating downstream human IL-15 coding and noncoding sequence in uppercase (human 3'UTR underscored), followed by an XhoI site in lowercase, followed by a lox site (uppercase, underscored), followed by sequence of the downstream neo selection cassette (uppercase), which extends 2.6 kb downstream.

FIG. 4 is a nucleic acid sequence (SEQ ID NO:3) that depicts the junction between the downstream portion of the neo selection cassette (uppercase), with lox site (uppercase and underscored), followed by an NheI site (lowercase), which is followed by mouse sequence downstream of the humanization (uppercase); the 2.6 kb indicates that the selection cassette extends further upstream; ellipses indicate that sequence continues.

FIG. 5 depicts an alignment of the protein sequences for the mouse IL-15 precursor protein (top, "mIL15_precursor," SEQ ID NO:4); the hybrid mouse/human IL-15 precursor protein (middle, "Regn_Hybrid_m/h," SEQ ID NO:5) produced by a humanization of the locus depicted in FIG. 1; and the known human IL-15 isoform 1 preproprotein (bottom, "hIL15 isoform 1," SEQ ID NO:6); the junction resulting from the humanization as depicted in FIG. 1 is indicated by a vertical arrow indicating C as the first amino acid of the replacement; the mature hIL-15 protein start is indicated by the bent arrow at the first amino acid N.

DETAILED DESCRIPTION

Figure 1:
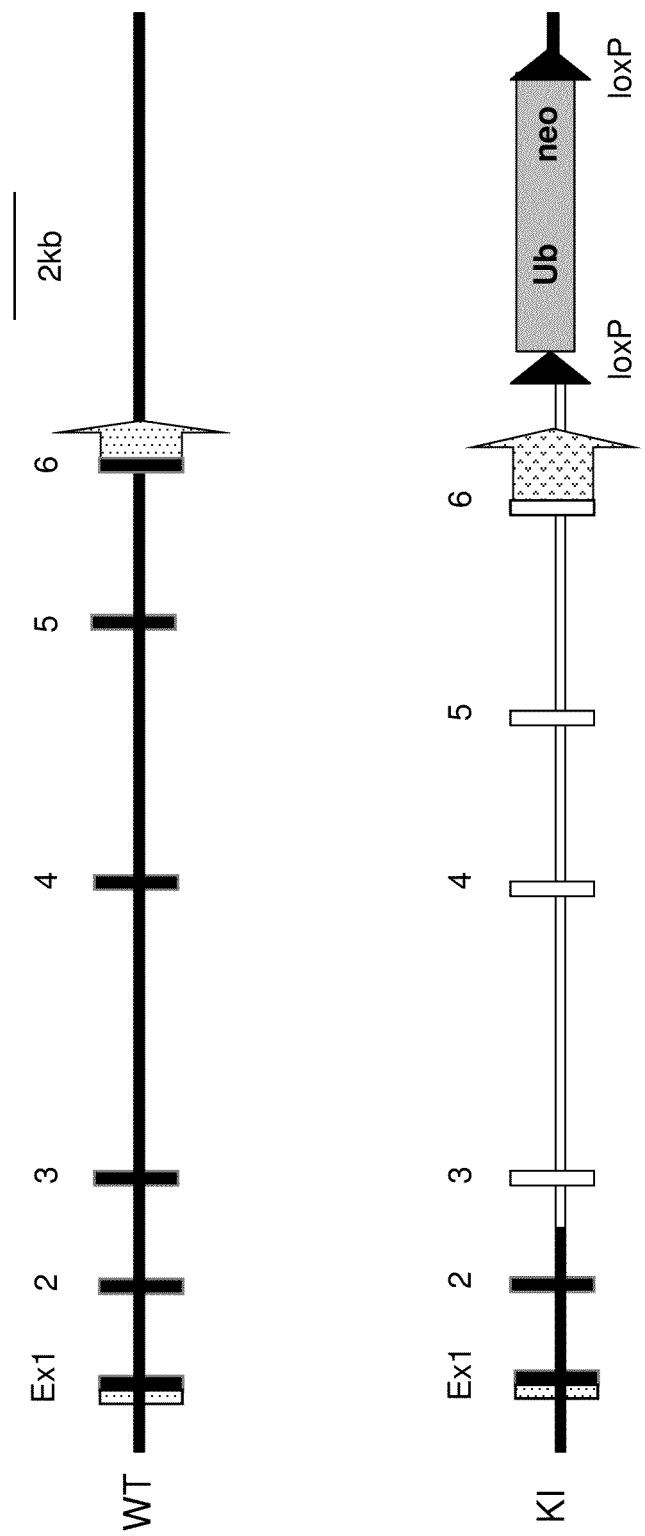
FIG. 1 depicts (not to scale) a schematic of a wild-type mouse IL-15 gene locus (top) and a humanized endogenous mouse IL-15 locus (bottom). Open symbols indicate human sequence; closed symbols indicate mouse sequence; stippled items indicate untranslated regions. Upstream (to the left in the figure) noncoding exons of the mouse IL-15 gene are not shown (and were not humanized). The bottom construct depicts an embodiment of a humanized IL-15 gene comprising a humanized 3'UTR (stippled) and a removable drug selection cassette, which is optionally removed in the humanized animal.

Genetically modified non-human organisms are provided that comprise a modified endogenous IL-15 locus that comprises a human sequence, e.g., a replacement of one or more non-human sequences with one or more human sequences. The organisms are generally able to pass the modification to progeny, i.e., through germline transmission. In particular, genetically modified non-human animals are provided.

The genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In yet another embodiment, the mouse is of a hybrid line (e.g., 50% BALB/c-50% 12954/Sv; or 50% C57BL/6-50% 129; e.g., F1H4 cells, see, e.g., Auerbach et al. (2000)).

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

The non-human animal may have one or more other genetic modifications, and/or other modifications, that are suitable for the particular purpose for which the humanized IL-15 mouse is made. For example, suitable mice for maintaining a xenograft (e.g., a human cancer or tumor), may comprise one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice may include, e.g., NOD mice, SCID mice, NON/SCID mice, IL2Rγ knockout mice, NOD/SCID/γc$^{null}$ mice (see, e.g., Ito, M. et al. (2002) NOD/SCID/γcnull mouse: an excellent recipient mouse model for engraftment of human cells, Blood 100(9):3175-3182), nude mice, and Rag1 and/or Rag2 knockout mice. These mice may optionally be irradiated, or otherwise treated to destroy one or more immune cell type. Thus, in various embodiments, a genetically modified mouse is provided that comprises a humanization of at least a portion of an endogenous non-human IL-15 locus, and further comprises a modification that compromises, inactivates, or destroys the immune system (or one or more cell types of the immune system) of the non-human animal in whole or in part. In one embodiment, modification is, e.g., selected from the group consisting of a modification that results in a NOD mice, a SCID mice, a NOD/SCID mice, an IL-2Rγ knockout mouse, a NOD/SCID/γc$^{null}$ mouse, a nude mice, a Rag1 and/or Rag2 knockout mice, and a combination thereof. In a specific embodiment, the mouse comprises a replacement of all mature IL-15-coding sequence with human mature IL-15 coding sequence.

In one embodiment, the mouse comprises a replacement of all mature IL-15-coding sequence with human mature IL-15 coding sequence, and the mouse is a NOD mouse. In one embodiment, the mouse comprises a replacement of all mature IL-15-coding sequence with human mature IL-15 coding sequence, and the mouse is a SCID mouse. In one embodiment, the mouse comprises a replacement of all mature IL-15-coding sequence with human mature IL-15 coding sequence, and the mouse is a NOD/SCID mouse. In one embodiment, the mouse comprises a replacement of all mature IL-15-coding sequence with human mature IL-15 coding sequence, and the mouse comprises an IL-2Rγ knockout. In one embodiment, the mouse comprises a replacement of all mature IL-15-coding sequence with human mature IL-15 coding sequence, and the mouse is a NOD/SCID/γc$^{null}$ mouse. In one embodiment, the mouse comprises a replacement of all mature IL-15-coding sequence with human mature IL-15 coding sequence, and the mouse is a nude mouse. In one embodiment, the mouse comprises a replacement of all mature IL-15-coding sequence with human mature IL-15 coding sequence, and the mouse comprises a Rag1 and/or Rag2 knockout.

Genetically modified non-human animals that comprise a modification of an endogenous non-human IL-15 locus, wherein the modification comprises a human nucleic acid sequence encoding at least a portion of a mature IL-15 protein, are provided. Although genetically modified cells are also provided that comprise the modifications described herein (e.g., ES cells, somatic cells), in many aspects and embodiments the genetically modified non-human animals comprise the modification of the endogenous IL-15 locus in the germline of the animal.

Genetically modified non-human animals that comprise a replacement of a non-human IL-15 gene sequence with a human IL-15 gene sequence are provided. In various embodiments, an endogenous non-human IL-15 locus is modified in whole or in part to comprise human nucleic acid sequence encoding at least one protein-coding exon of a mature IL-15 protein. In various embodiments, the human sequence is a human genomic sequence, e.g., a contiguous human genomic sequence comprising one or more exons that encode a portion of a mature IL-15 protein, or, e.g., a cDNA that encodes at least one or more exons that encode a portion of a mature IL-15 protein. In various embodiments, all IL-15 protein-coding exons that encode protein sequences that appear in a mature human IL-15 protein are humanized. In various embodiments, the humanized IL-15 locus is under control of upstream endogenous regulatory sequences (e.g., all endogenous sequences upstream of the humanization). In various embodiments, the humanization comprises a human 3'UTR.

In various embodiments, the non-human animals are mammals. In certain embodiments, the mammals are rodents. Rodents that comprise a humanization of an IL-15 gene, at an endogenous rodent IL-15 locus, are provided. Methods for making rodents, e.g., mice, that comprise a replacement of an endogenous IL-15 gene or fragment thereof (e.g., a fragment comprising one or more exons) with a humanized IL-15 gene, or fragment thereof (e.g., a fragment comprising one or more exons), at the endogenous IL-15 locus. Cells, tissues, and mice are provided that comprise the humanized gene are provided, as well as cells, tissues, and mice that express human IL-15 from an endogenous non-human IL-15 locus. Rodents that express a human IL-15 protein under control of an endogenous rodent promoter are also provided.

IL-15 was discovered as an IL-2-independent T cell growth factor that stimulates T cell proliferation and supports thymic development and natural killer (NK) cell development (Burton, J. D. t al. (1994) A lymphokine, provisionally designated interleukin T and produced by a human adult T-cell leukemia line, stimulates T-cell proliferation and the induction of lymphokine-activated killer cells, Proc. Natl. Acad. Sci. USA 91:4935-4939; Grabstein, K. H. et al. (1994) Cloning of a T Cell Growth Factor That Interacts with the β Chain of the Interleukin-2 Receptor, Science 264:965-968). IL-2 and IL-15 share receptor subunits. However, the independent importance of IL-15 in maintenance of immune cell populations is undisputed; IL-15/IL-15R knockout mice exhibit low CD8+ T cells, low memory CD8+ T cells, and low NK cells, as well as other cell types (reviewed in Steel, J. C. et al. (2012) Interleukin-15 biology and its therapeutic implications in cancer, Trends in Pharmacological Sciences, 33(1):35-41).

IL-15 is known to be expressed in endothelial cells; IL-15 derived from endothelial cells stimulates transendothelial migration of T cells (see, Oppenheimer-Marks, N. (1998) Interleukin 15 is Produced by Endothelial Cells and Increases the Transendothelial Migration of T Cells in Vitro and in the SCID Mouse-Human Rheumatoid Arthritis Model In Vivo, J. Clin. Invest. 101(6):1261-1272). Thus, early work established a likelihood that T cell recruitment to inflammatory sites is mediated by IL-15 (Id.). This fact is significant, because improper or over-expression of IL-15 may readily lead to a pathological phenotype—a situation faced with transgenic non-human animals that express dysregulated IL-15. Proper IL-15 regulation is important, because IL-15 is believed to be a pro-inflammatory cytokine that is at the apex of a pro-inflammatory cytokine cascade, preceding expression of many inflammation mediators (McInnes, I. B. et al. (1997) Interleukin-15 mediates T cell-dependent regulation of tumor necrosis factor-α production in rheumatoid arthritis, Nature Med. 3:189-195, quoted in Waldmann, T. A. (2006) The biology of interleukin-2 and interleukin-15: implications for cancer therapy and vaccine design, Nature Rev. Immunol. 6:595-601).

Transgenic mice expressing human IL-15 under control of an enterocyte-specific promoter (T3b promoter) to express human IL-15 in intestinal epithelial cells develop spontaneous inflammation in the duodeno-jejunal area (Yokoyama, S. et al. (2008) Antibody-mediated blockade of IL-15 reverses the autoimmune intestinal damage in transgenic mice that overexpress IL-15 in enterocytes, Proc. Natl. Acad. Sci. USA 106(37)15849-15854; Ohta, N. et al. (2002) IL-15-dependent activation-induced cell death-resistant Th1 type CD8 alpha beta+NK1.1+ T cells for the development of small intestinal inflammation, J. Immunol. 169:460-468). See, also, Nishimura, H. et al. (2005) A novel autoregulatory mechanism for transcriptional activation of the IL-15 gene by nonsecretable isoform of IL-15 generated by alternative splicing, FASEB J. 19:19-28 (transgenic mice with a randomly inserted mIL-15 gene variant).

Mice transgenic for a secretable isoform of IL-15 under control of an MHC class I promoter have been prepared, but they overexpress IL-15 (Yajima, T. et al. (2001) Memory phenotype CD8(+) T cells in IL-15 transgenic mice are involved in early protection against a primary infection with Listeria monocytogenes, Eur. J. Immunol. 31(3):757-766). Overexpression of IL-15 is correlated with destruction of intestinal epithelium by IL-15-activated cytotoxic T lymphocytes in celiac disease (Yokoyama, S. et al. (2011) Transgenic Mice that Overexpress Human IL-15 in Enterocytes Recapitulate Both B and T Cell-Mediated Pathologic Manifestations of Celiac Disease, J. Clin. Immunol. 31:1038-1044), presumably due to promoting proliferation of CD8+ T cells that target enterocytes through NKG2D (natural killer group 2, member D)—mediated process that include cognate receptors such as MICA/B (Id., at 1039). It seems clear by now that locally-expressed IL-15 causes T cell-mediated tissue damage in the intestine in celiac disease (Id.).

At least one study of transgenic mice that are engineered to overexpress IL-15 in muscle tissue and in circulation (employing a skeletal muscle promoter) establish that IL-15 overexpression affects metabolism; such mice appear to employ IL-15 as a myokine that reduces body fat and provides resistance to diet-induced adiposity (Quinn, L. S. et al. (2009) Oversecretion of interleukin-15 from skeletal muscle reduces adiposity, Am. J. Physiol. Endocrinol. Metab. 296:E191-E202).

IL-15 is also thought to be implicated in rheumatoid arthritis, perhaps through abnormal T-cell infiltration of joints (reviewed in, e.g., Fehninger T. A. and Caligiuri, M. A. (2001) Interleukin 15: biology and relevance to human disease, Blood 97(1):14-32). Sarcoidosis patients also produce alveolar macrophages that express IL-15, which may mediate T-cell proliferation in lung (Id., at 23). IL-15 may also mediate organ rejection in allografts via proliferation of T cells (Id., at 24). IL-15 may also be implicated in adult T-cell leukemia (e.g., HTLV-1-mediated), based at least in part on the activation of IL-15-mediated pathways in patients with adult T-cell leukemia (Id.). In vitro work suggests that IL-15 activates HIV replication, which may be the case in humans as well (Id., at 25).

In transgenic mice that express IL-15 driven by an MHC class I promoter infected with *Mycobacterium bovis bacillus* Calmette-Guérin, overproduction of IL-15 rendered the mice susceptible to LPS-induced lethal liver injury, an effect that was not observed when CD8+ T cells were depleted from the mice (Yajima, T. (2004) Overexpression of Interleukin-15 Increases Susceptibility to Lipopolysaccharide-Induced Liver Injury in Mice Primed with *Mycobacterium bovis Bacillus* Calmette-Guérin, Infection and Immunity 72(7): 3855-3862), suggesting an effect mediated by IL-15 overproduction.

Transgenic mice that express IL-15 driven by a skeletal muscle promoter exhibited a higher insulin sensitivity and a resistance to diet-induced obesity, and appeared to promote fatty acid metabolism (Quinn, L. S. et al. (2011) Overexpression of interleukin-15 in mice promotes resistance to diet-induced obesity, increased insulin sensitivity, and markers of oxidative skeletal muscle metabolism, International Journal of Interferon, Cytokine and Mediator Research, 3:29-42).

Selective blockade of murine IL-15 has been studied, including a soluble IL-15Rα, which may be of clinical benefit in controlling rheumatoid arthritis (Id., at 27). Thus, non-human animals that express human or humanized IL-15, including in a physiologically relevant fashion, are useful for assessing or identifying selective blockers of human IL-15. According to one reviewer, "the development of effective human IL-15 blocking agents . . . with in vivo blocking activity could facilitate rapid translation of such approaches to the clinic" (Id., at 27). Thus, genetically modified non-human animals, e.g., non-human animals that comprise a human IL-15 gene in their germline, wherein the non-human animals express human IL-15 in a physiologically appropriate manner, would be quite useful.

IL-15 is a pleiotropic cytokine that is required for NK cell development and function and T cell homeostasis. It is particularly important for the memory CD8+ T cell compartment. IL-15 is produced primarily by dendritic cells and macrophages, and is transpresented via IL-15/IL-15R complex to NK cells and T cells. IL-15 is also known to be a pro-inflammatory cytokine that induces production of other cytokines, recruits and activates T-cells and other inflammatory cells, promotes development and survival of NK cells, and promotes angiogenesis; and many of these features are displayed in psoriatic lesions (reviewed and reported in Villadsen, L. S. (2003) Resolution of psoriasis upon blockade of IL-15 biological activity in a xenograft mouse model, J. Clin. Invest. 112(10):1571-1580). It has been proposed that IL-15 is at the apex of the pro-inflammatory cytokine cascade, with various strategies under way to modulate IL-15 signalling for disease treatment (reviewed in Waldman (2006) The biology of interleukin-2 and interleukin-15: implications for cancer therapy and vaccine design, Nature Reviews Immunology, 6:595-601). In a xenograft mouse model of psoriasis in SCID mice, blockade of IL-15 using an antibody to IL-15R (or IL-15) resulted in reduction of severity of psoriasis (Id.). Thus, non-human animals that express IL-15 in a physiologically relevant manner are useful (e.g., have a well-established utility) in models for human diseases, including but not limited to models in immune-compromised mice, such as, e.g., SCID mice and other immune-compromised mice. Thus, in one embodiment, a rodent (e.g., a mouse) comprising a human or humanized IL-15 gene under control of endogenous non-human regulatory elements (e.g., a humanization of the coding gene for IL-15 in a rodent, e.g., a mouse) is provided.

The IL-15 gene is found on human chromosome 4831 and on mouse chromosome 8. The human gene contains 8 exons (7 coding), and appears to exist in two isoforms in both humans and mice (see, e.g., Fehninger T. A. and Caligiuri, M. A. (2001) Interleukin 15: biology and relevance to human disease, Blood 97(1):14-32). mRNA for IL-15 is produced in a wide variety of tissues and cell types, and regulation of the IL-15 gene in humans appears to be negatively regulated by an upstream region whose deletion results in a dramatic increase in IL-15 promoter activity (Id., at 17). Transgenic mice that lack posttranscriptional control of IL-15 exhibit a fatal lymphocytic leukemia (Id.). Regulation of IL-15 expression appears to be very tight, mediated at least by 5' untranslated region AUG triplets, 3' regulatory elements, and a putative C-terminal region regulatory site (reviewed in McInnes, I. B. and Gracie, J. A. (2004) Interleukin-15: a new cytokine target for the treatment of inflammatory diseases, Current Opinion in Pharmacology 4:392-397). The human IL-15 gene has nine exons and eight introns, which includes an exon 4a that is present in humans but not mice, though the mature IL-15 protein is encoded by just exons 5 through 8 (reviewed in Budagian, V. et al. (2006) IL-15/IL-15 receptor biology: A guided tour through an expanding universe, Cytokine & Growth Factor Reviews 17:259-280). There are two alternatively spliced mRNA products that produce two IL-15 isoforms, which differ only in the length of signal peptide, which is true for both mouse and human proteins (see, e.g., Id.). FIG. 1, which depicts a humanization strategy for a mouse IL-15 locus, omits upstream mouse sequences that were not humanized (including exons that do not appear in the mature protein) for simplicity, and presents a re-numbering of exons relevant to the humanization shown.

IL-15 is expressed in many cell types and tissues, including monocytes, macrophages, dendritic cells, keratinocytes, epidermal cells, fibroblasts, and epithelial cells of nerve, kidney, placenta, lung, heart, and muscle (Grabstein, K. H. et al. (1994) Cloning of a T Cell Growth Factor That Interacts with the β Chain of the Interleukin-2 receptor, Science 264:965-968).

Mouse IL-15 coding sequences were humanized as depicted in FIG. 1, which omits depiction of two non-coding exons (which were not humanized) far upstream from the coding exons. 12299 nucleotides of mouse sequence was replaced by 12896 nucleotides of human sequence to humanize the IL-15 gene.

In one embodiment, the humanized IL-15 locus lacks a human IL-15 5'UTR. In one embodiment, the humanized IL-15 locus comprises a rodent 5'UTR. In a specific embodiment, the rodent is a mouse, and the humanized IL-15 locus comprises a mouse IL-15 5'UTR.

Rodents that express human or humanized IL-15 protein, e.g., in a physiologically appropriate manner, provide a variety of uses that include, but are not limited to, developing therapeutics for human diseases and disorders. IL-15 antagonists, such as, e.g., soluble forms or IL-15 receptor, can prevent development of collagen-mediated arthritis in an animal model (see, Ruchatz, H. et al., (1998) Soluble IL-15 receptor α-chain administration prevents murine collagen-induced arthritis: a role for IL-15 in development of antigen-induced immunopathology, J. Immunol. 160:5654-5660;); anti-IL-15 antibodies have exhibited efficacy against a variety of diseases, including psoriasis and rheumatoid arthritis; in an animal model of arthritis, an IL-15 receptor antagonist prevents both the development and progression of arthritis, as well as reducing lymphocyte infiltration of joints (Ferrari-Lacraz, S. et al. (2004) Targeting IL-15 Receptor-Bearing Cells with an Antagonist Mutant IL-15/Fc Protein Prevents Disease Development and Progression in Murine Collagen-Induced Arthritis, J. Immunol. 173:5815-5826); IL-15-mediated signaling has also been implicated in IBD, SLE, inflammatory synovitis, diabetes mellitus, and asthma (reviewed in Budagian, V. et al. (2006) IL-15/IL-15 receptor biology: A guided tour through an expanding universe, Cytokine & Growth Factor Reviews 17:259-280).

Studies with IL-15 knockout mice establish that IL-15 is necessary for the development of certain immune cells, in particular, NK cells (reviewed in Lodolce, J. P. (2002) Regulation of lymphoid homeostasis by interleukin-15, Cytokine & Growth Factor Reviews, 13:429-439). Indeed, IL-15 knockout mice do not long survive exposure to certain pathogens (e.g., Vaccinia virus), presumably due to lack of NK and CD8+ T cells (Id.). Thus, effects of hIL-15 antagonists on human NK cell function represent an important application of a humanized IL-15 animal.

In various aspects, genetically modified animals are provided that express human or humanized IL-15, which are useful for testing antagonists to human IL-15. The genetically modified animals may further comprise an animal model of a human disease, e.g., the disease is induced genetically (a knockin or knockout) or otherwise. In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

EXAMPLES

Example 1

Humanizing the Mouse IL-15 Locus

Mouse ES cells were modified to replace certain mouse IL-15 gene sequences with certain human IL-15 gene sequences at the endogenous mouse IL-15 locus, under control of mouse IL-15 regulatory elements, using VELOCIGENE® genetic engineering technology, to produce a humanized locus as shown in FIG. 1. FIG. 1 does not show upstream (with respect to direction of transcription of the IL-15 gene) the 5' untranslated exons of the mouse gene; Ex1 of FIG. 1 shows a small untranslated region (unfilled) upstream of coding exon. As shown the humanization at the bottom of FIG. 1, mouse coding exons 1 and 2 were retained, whereas mouse coding exons 3 through 6 were replaced with human exons 3 through 6. At the downstream end, human exon 6 is followed by a stop codon and a human 3'-UTR, and further by human sequence found downstream of the human 3'UTR. For selection purposes, a selection cassette (floxed for removal by Cre) was included. The humanized locus of FIG. 1 expresses a mature IL-15 protein that is fully human.

Targeting Construct. Bacterial homologous recombination (BHR) is performed to construct a large targeting vector (LTVEC) containing sequences of the human IL-15 gene for targeting to the mouse IL-15 locus using standard BHR techniques (see, e.g., Valenzuela et al. (2003) High-throughput engineering of the mouse genome coupled with high-resolution expression analysis, Nature Biotech. 21(6):652-659) and gap repair BHR. Linear fragments are generated by ligating PCR-generated homology boxes to cloned cassettes followed by gel isolation of ligation products and electroporation into BHR-competent bacteria harboring the target bacterial artificial chromosome (BAC). Mouse BAC PRCI23-203P7 is used as the source of mouse sequence; human BAC RP11-103B12 is used as the source of human IL-15 gene sequence. Following a selection step, correctly recombined clones are identified by PCR across novel junctions, and by restriction analysis. A large targeting vector (LTVEC) containing homology arms and human IL-15 gene sequences was made. Mouse ES cells were electroporated with the LTVEC constructs, grown on selection medium, and used as donor ES cells to make humanized IL-15 mice comprising a replacement at the endogenous mouse IL-15 locus with human sequence as depicted in FIG. 1.

The mouse IL-15 gene (mouse GeneID: 103014; RefSeq transcript: NM_008357.2; ensemble eID:16168) is modified by using genomic coordinates for deletion GRCM38: ch 8: 82331173-82343471(minus strand); genomic coordinates for replacement GRCh37: ch4: 142642924-142655819 (plus strand). 12299 nucleotides of mouse sequence was replaced by 12896 nucleotides of human sequence. The replacement of mouse IL-15 sequence as described above is graphically presented in FIG.1.

The LTVEC comprising the humanized IL-15 gene had about 13 kb of upstream mouse targeting arm flanked upstream with a MluI site, and a 27 kb downstream mouse targeting arm flanked downstream with an AscI site. The LTVEC was linearized with MluI and AscI for electroporation.

Following construction of the LTVEC, nucleotide sequence of the LTVEC across the mouse/human 5' junction, and human/mouse 3' junction is as shown in FIGS. 2-4.

Following electroporation of the ES cell, a loss of native allele assay (see, e.g., Valenzuela et al. (2003)) is performed to detect loss of endogenous IL-15 sequence due to the targeting.

Correctly targeted ES cells (MAID 5217) were further electroporated with a transient Cre-expressing vector to remove the Neo drug selection cassette. The resultant cassette-deleted ES cells were designated MAID 5218.

Example 2

Humanized IL-15 Mice

Generating Humanized IL-15 Mice. Donor mouse ES cells comprising a humanized IL-15 locus (e.g., MAID 5217 or MAID 5218) are introduced into early stage mouse embryos by the VELOCIMOUSE® method (Poueymirou et al. (2007) F0 generation mice fully derived from gene-targeted embryonic stem cells allowing immediate phenotypic analyses, Nat Biotechnol 25:91-99). Heterozygous mice are obtained, and to obtain homozygotes with respect to humanized IL-15, heterozygotes are bred.

Example 3

Phenotyping Humanized IL-15 Mice

Mice. Mice were either wild-type (WT) 8-10 week old Balb/c females or age-matched MAID 5217 (heterozygous for human IL-15 gene) females. Alternatively, mice were either wild-type (WT) or age-matched MAID 5217 or MAID 5218 (both heterozygous for the human IL-15 gene) mice.

In Vivo Poly I:C injection. WT Balb/c or MAID 5217 het were injected with 50 µg poly I:C (Invivogen; Cat # tlrl-pic)

via tail-vein (IV injection). After 24 hours, mice were sacrificed and bled via cardiac puncture and serum isolated. Spleens were also harvested and splenocytes prepared by mechanically disrupting spleens through a 70 μM mesh filter followed by ACK lysis buffer (Invitrogen) treatment to lyse red blood cells (RBCs). Isolated splenocytes were cultured for additional stimulation (see below). Serum was analyzed for human IL-15 using the R&D Systems human IL-15 QUANTIKINE™ kit. WT or MAID 5218 het mice were injected with 50 μg poly I:C (Invivogen; Cat # tlrl-pic) via IP. Mice were bled the next day via cardiac puncture and serum was analyzed for human IL-15 by ELISA (R&D Systems QUANTIKINE™ ELISA kit).

Bone Marrow-Derived Dendritic Cell (BM-DC) Preparation. Bone marrow was flushed from the tibia of non-injected mice and RBCs lysed with ACK lysis buffer. Cells were washed with RPMI complete (w/HEPES, Gentamicin, sodium pyruvate, L-glutamine, and non-essential amino acids)+10% fetal bovine serum (FBS) and counted. $2 \times 10^6$ cells were cultured per well in a 6-well plate with 3 mL/well of RPMI complete+10% FBS+50 ng/mL murine GM-CSF+ 50 ng/mL murine IL-4. Cells were cultured at 370 C/5% CO2 and given fresh GM-CSF/IL-4 at days 2 and 4 of culture. At day 5 of culture, non-adherent BM-DCs were harvested from the cultures and respective culture media saved (conditioned media).

Splenocyte Culture. Spleens were harvested from respective mice and splenocytes prepared by mechanically disrupting spleens through a 70 μM mesh filter followed by ACK lysis buffer (Invitrogen) treatment to lyse RBCs. Isolated splenocytes were cultured in a 48-well plate at $2 \times 10^6$/mL splenocytes in 1 mL of RPMI complete+10% FBS. Cells were treated with 10 μg/mL poly I:C, 10 μg/mL PMA or left untreated. Cells were cultured as such overnight and the next day supernatant harvested and concentrated 8-fold using Amicon 2 mL filters with 3 kd molecular weight cut-off (MWCO). Concentrated supernatants were analyzed for human IL-15 using the R&D systems human IL-15 QUANTIKINE™ kit.

BM-DC Culture. $2 \times 10^6$/mL BM-DCs were plated in a 24-well plate in 0.5 mL of fresh RPMI complete+10% FBS and 0.5 mL of conditioned media. Cells were treated with 25 μg/mL poly I:C, 1 μg/mL LPS or left untreated. All conditions were performed in duplicate. Cells were cultured as such for 36 hrs and then the supernatant harvested. Supernatants were concentrated 7-fold using Amicon 2 mL filters with 3 kd MWCO. Human IL-15 levels in concentrated supernatants were analyzed using the R&D systems human IL-15 QUANTIKINE™ kit. RNA was isolated from cells via RNAeasy™ mini prep kit from Qiagen for RT-PCR analysis of human IL-15 transcript levels.

ELISA. R&D systems human IL-15 QUANTIKINE™ kit was used to measure human IL-15 in serum and concentrated splenocytes or BM-DC supernatants. Kit was used according to manufacturer's instructions. Additional controls were performed to validate this kit for specificity (only detects human, not mouse, IL-15) and to confirm it does not react to poly I:C. Therefore, 1000 pg/mL of murine IL-15 was run on the ELISA (note: highest standard for the human IL-15 is 250 pg/mL) and poly I:C alone at 25 μg/mL and 12.5 μg/mL. The kit was found to react specifically to human IL-15 (no detection of mouse IL-15) and did not react to poly I:C.

RT-PCR. cDNA was prepared from ~200 ng of isolated RNA using SUPERSCRIPT™ III First-strand synthesis system for RT-PCR kit (Invitrogen) according to manufacturer's instructions. Specific human IL-15 transcript was amplified via using Taqman DNA polymerase with the following primers: hIL-15 Forward primer: gtaaraagtg atttgaaaaa aattgaagat (SEQ ID NO:7); hIL-15 Reverse primer: tacaaaactc tgcaaaaatt ctttaatat (SEQ ID NO:8). PCR reaction was performed with 40 cycles of the following: denaturing at 940 C for 15 seconds, annealing at 60° C. for 30 seconds, extending at 72° C. and reaction then kept at 4° C. Transcript was run on a 1% agarose gel using Promega 6× loading dye.

Figure 6:
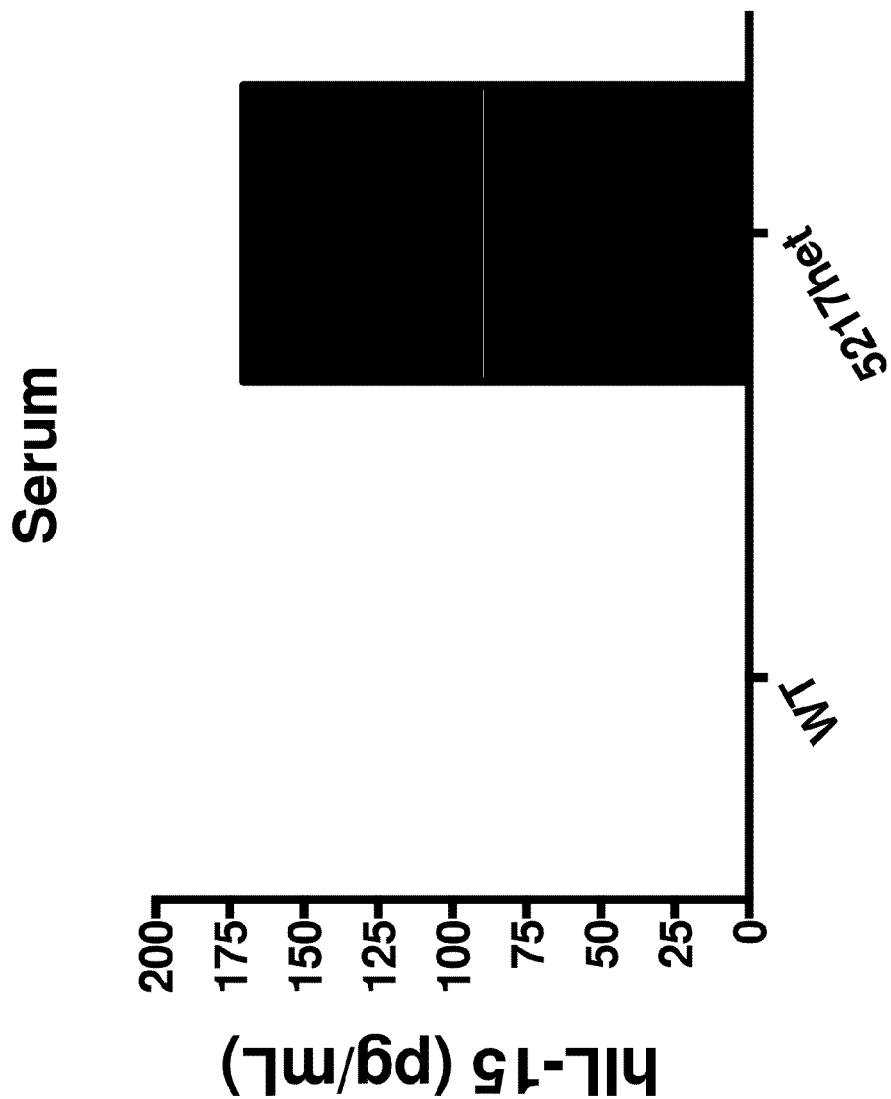
FIG. 6 depicts IL-15 detected in serum from poly I:C injected heterozygous hIL-15 mice. The control indicates that no hIL-15 was detected in cultured splenocytes from poly I:C injected wild-type mice.
Figure 7:
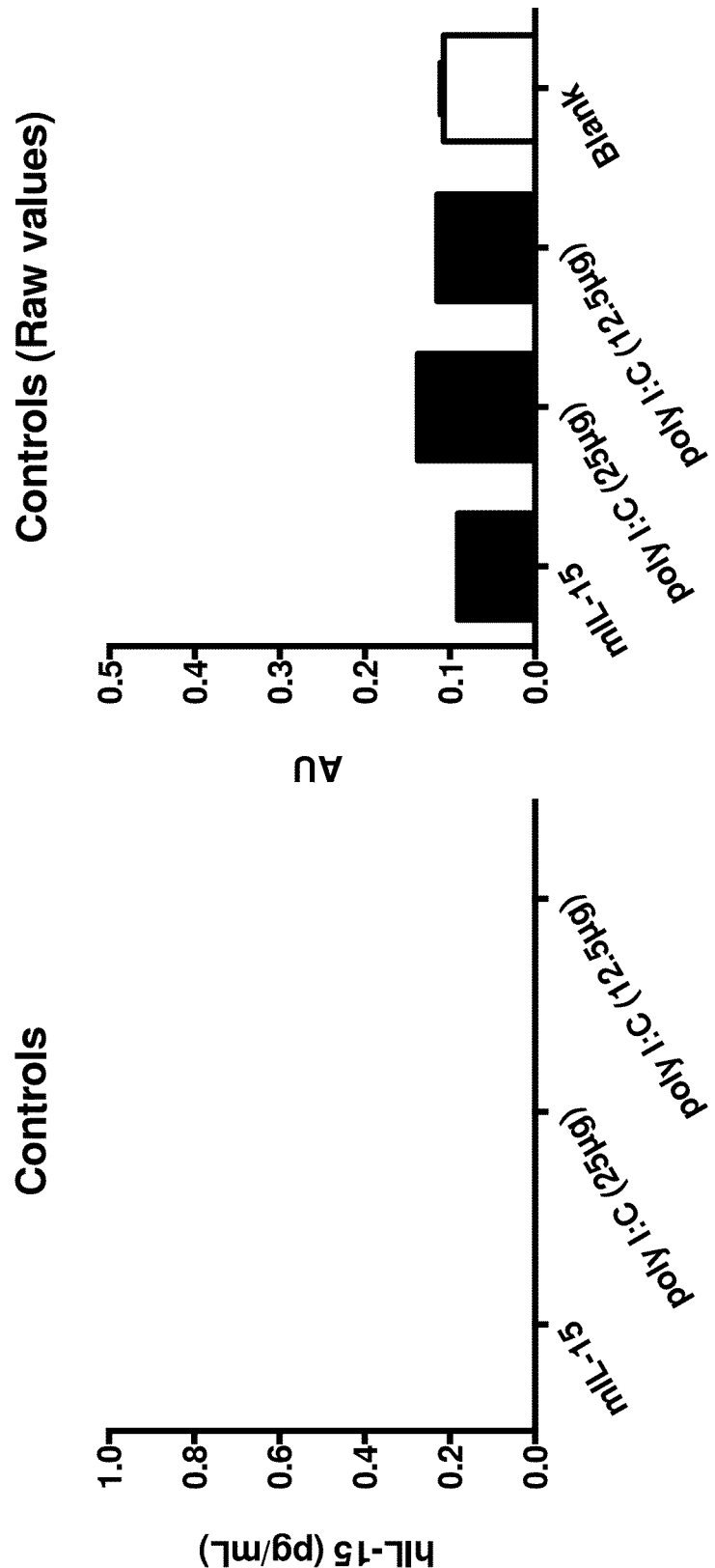
FIG. 7 depicts that human IL-15 does not react with mouse IL-15 or poly I:C in an ELISA assay. Mouse IL-15 was at 1000 pg/mL.
Figure 8:
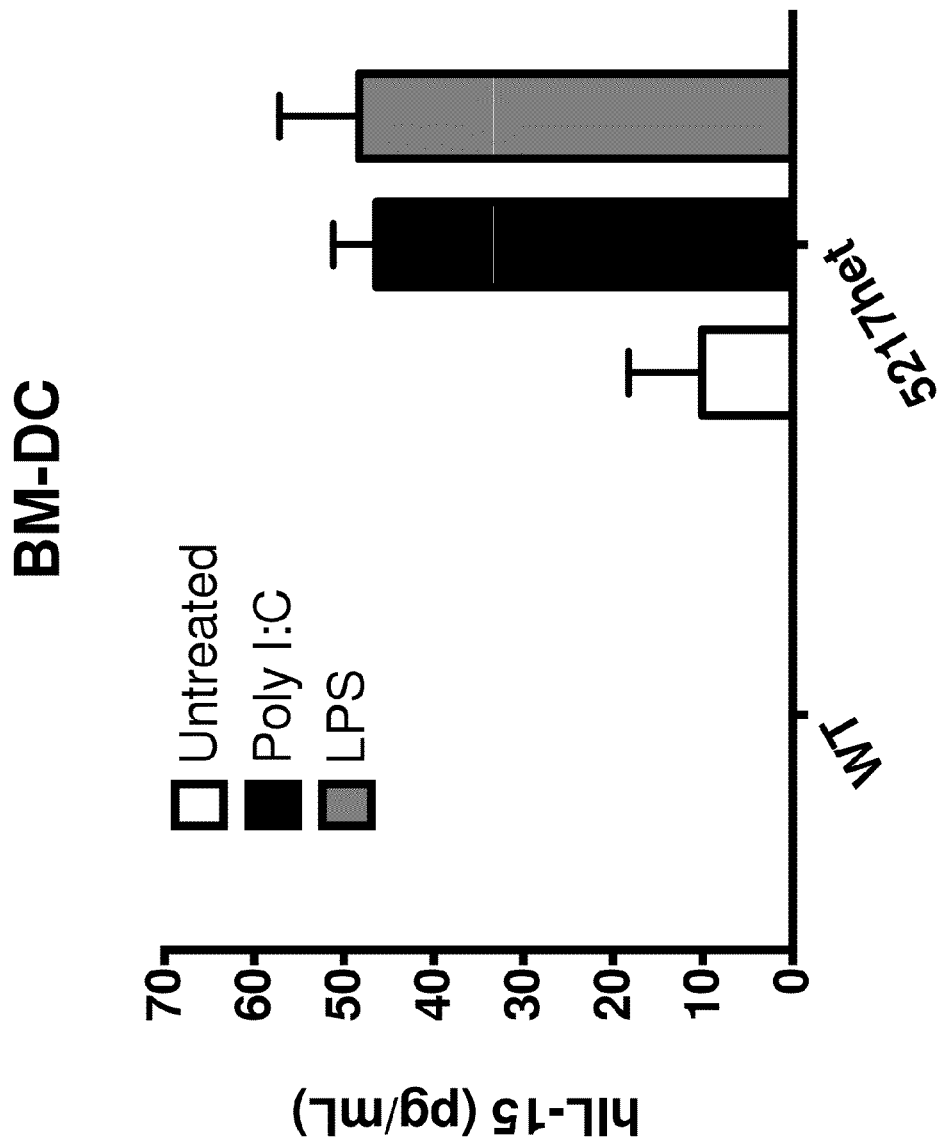
FIG. 8 depicts BM-DCs from mice heterozygous for human IL-15, using 7-fold concentrated BM-DC supernatants for untreated mice, poly I:C treated mice, and LPS treated mice.
Figure 9:
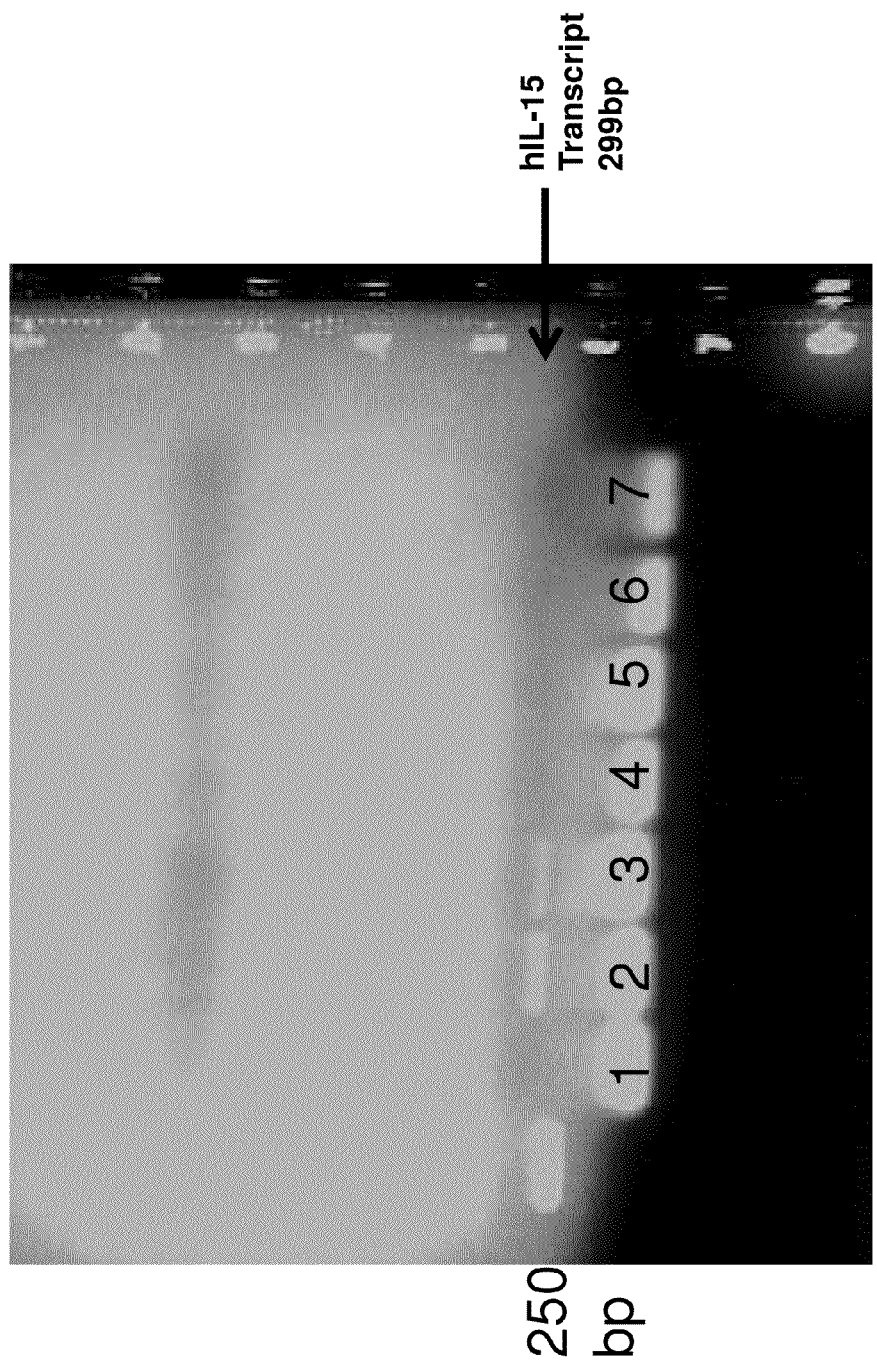
FIG. 9 depicts that BM-DCs from mice heterozygous for human IL-15 produce human IL-15 transcript (RT-PCR data). Lane 1: untreated mice; Lane 2: poly I:C treated mice; Lane 3: LPS only; Lane 4: wild-type untreated mice; Lane 5: wild-type poly I:C treated mice; Lane 6: wild-type LPS treated mice; Lane 7: no cDNA control (water only).
Figure 10:
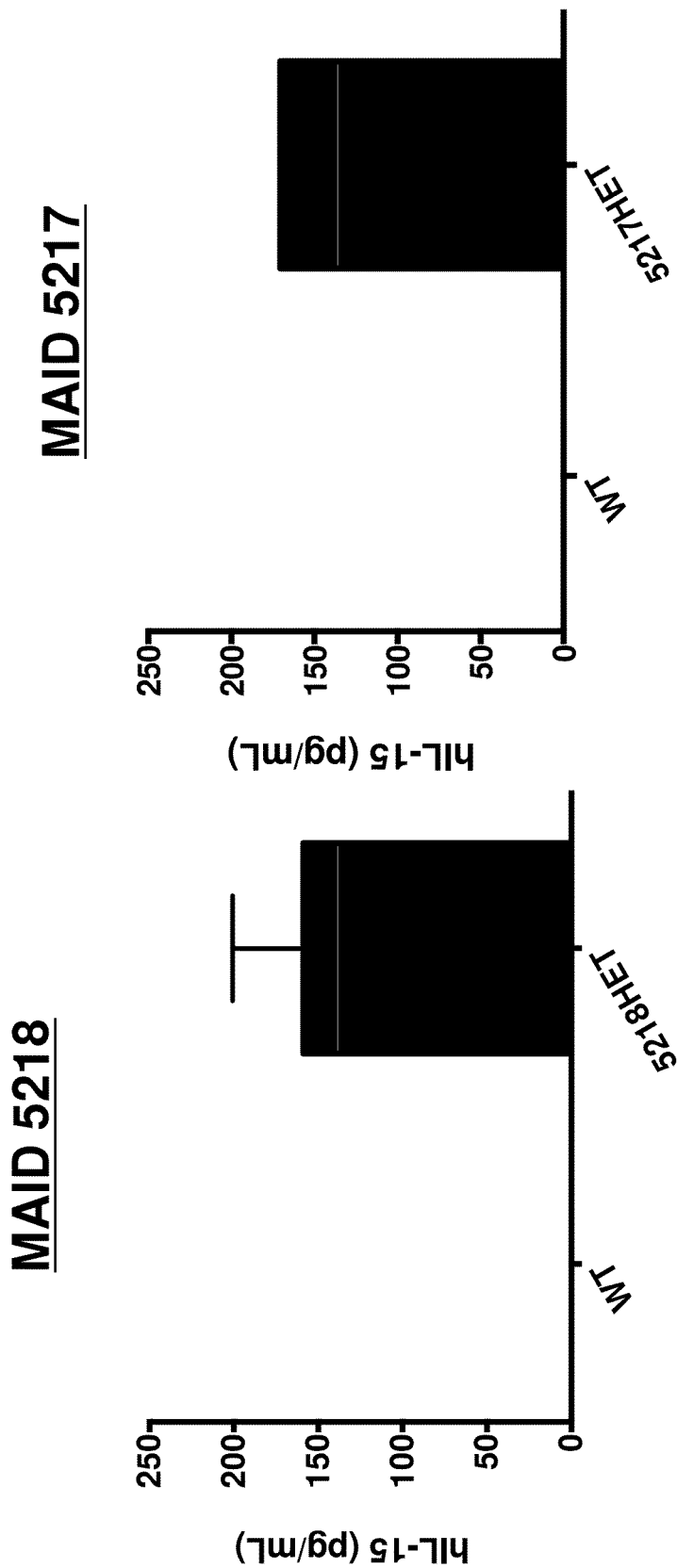
FIG. 10 depicts that MAID 5218 het mice produced human IL-15 upon poly I:C injection at a level comparable to MAID 5217 het mice.

Results. Human IL-15 was observed in serum of poly I:C-injected MAID 5217 het, but not in a poly I:C-injected age/sex-matched WT Balb/c mouse (FIG. 6; and FIG. 10, right panel). Similarly, human IL-15 was observed in serum of poly I:C-injected MAID 5218 het, but not in a poly I:C-injected age/sex-matched WT mouse (FIG. 10, left panel). The level of IL-15 produced in MAID 5218 was comparable to MAID 5217 (FIG. 10). PMA-stimulated splenocytes from MAID 5217 secrete low levels of human IL-15 in vitro (none observed in splenocytes from WT mice).

Additionally, BM-DCs derived from MAID 5217 het demonstrate human IL-15 secretion upon in vitro stimulation with poly I:C (TLR3 agonist) and LPS (TLR4 agonist), as well as significant basal levels. RT-PCR analysis demonstrated specific human IL-15 transcript only in BM-DCs from MAID 5217 het mice.

Overall, the data indicates that MAID 5217 het and MAID 5218 het expresses human IL-15.

Example 4

Mouse Homozygous for Human IL-15

Heterozygous mice are bred, then genotyped as described above. Homozygous hIL-15 mice are maintained by inbreeding.

What is claimed is:

1. A genetically modified mouse whose genome comprises a replacement at an endogenous mouse IL-15 locus of a mouse genomic segment comprising sequences of mouse exons 3, 4, 5 and 6 coding for a mature mouse IL-15 polypeptide with a human genomic segment comprising human IL-15 exons coding for a mature human IL-15 polypeptide to form a humanized IL-15 gene, wherein the human IL-15 exons in said human genomic segment consist of human exons 3, 4, 5 and 6, wherein the humanized IL-15 gene is under control of endogenous mouse IL-15 upstream regulatory elements at the endogenous mouse IL-15 locus, and wherein the genetically modified mouse comprises a human IL-15 polypeptide in serum following treatment of said mouse with Poly I:C.

2. The genetically modified mouse of claim 1, wherein the humanized IL-15-encoding gene encodes a protein which comprises the amino acid sequence of SEQ ID NO: 5.

3. A method of making a genetically modified mouse, comprising modifying the genome of a mouse by replacing at an endogenous mouse IL-15 locus of a mouse genomic segment comprising sequences of mouse exons 3, 4, 5 and 6 coding for a mature mouse IL-15 polypeptide with a human genomic segment comprising human IL-15 exons coding for a mature human IL-15 polypeptide to form a humanized IL-15 gene, wherein the human IL-15 exons in said human genomic segment consist of human exons 3, 4, 5 and 6, wherein the humanized IL-15 gene is under control of endogenous mouse IL-15 upstream regulatory elements at the endogenous mouse IL-15 locus, and wherein the genetically modified mouse comprises a human IL-15 polypeptide in serum following treatment of said genetically modified mouse with Poly I:C.

4. The method of claim 3, wherein the humanized IL-15-encoding gene encodes a protein which comprises the amino acid sequence of SEQ ID NO: 5.

* * * * *

UNITED STATES PATENT AND TRADEMARK OFFICE
CERTIFICATE OF CORRECTION

| | | |
|---|---|---|
| PATENT NO. | : 9,155,290 B2 | Page 1 of 1 |
| APPLICATION NO. | : 14/514454 | |
| DATED | : October 13, 2015 | |
| INVENTOR(S) | : Rojas et al. | |

It is certified that error appears in the above-identified patent and that said Letters Patent is hereby corrected as shown below:

On the title page item (72) under Inventors add --Cagan Gurer--.

Signed and Sealed this
Tenth Day of May, 2016

Michelle K. Lee
*Director of the United States Patent and Trademark Office*

SEQUENCE LISTING

<160> NUMBER OF SEQ ID NOS: 8

<210> SEQ ID NO 1
<211> LENGTH: 208
<212> TYPE: DNA
<213> ORGANISM: Artificial Sequence
<220> FEATURE:
<223> OTHER INFORMATION: Synthetic Oligonucleotide

<400> SEQUENCE: 1
atccatttag cctttctctg atcactaagt tggacagttg gacagtcttc ctcaaattag      60

```
cttagactat caaaattata ctgtattttt ggtatttcca gcgatcgctt cagttacaag    120
gctgttgaat gcacagaagc aaggataaca ctgatttttt cactggtcag aataaaaatt    180
attgattgct cttttgctta tagtattc                                       208
```

<210> SEQ ID NO 2
<211> LENGTH: 2029
<212> TYPE: DNA
<213> ORGANISM: Artificial Sequence
<220> FEATURE:
<223> OTHER INFORMATION: Synthetic Oligonucleotide
<400> SEQUENCE: 2

```
aatgtaacag aatctggatg caaagaatgt gaggaactgg aggaaaaaaa tattaaagaa     60
tttttgcaga gttttgtaca tattgtccaa atgttcatca acacttcttg attgcaattg    120
attcttttta aagtgtttct gttattaaca aacatcactc tgctgcttag acataacaaa    180
acactcggca tttcaaatgt gctgtcaaaa caagtttttc tgtcaagaag atgatcagac    240
cttggatcag atgaactctt agaaatgaag gcagaaaaat gtcattgagt aatatagtga    300
ctatgaactt ctctcagact tactttactc attttttttaa tttattattg aaattgtaca    360
tatttgtgga ataatgtaaa atgttgaata aaaatatgta caagtgttgt ttttttaagtt    420 gcactgatat tttacctctt attgcaaaat agcatttgtt taagggtgat agtcaaatta    480
tgtattggtg gggctgggta ccaatgctgc aggtcaacag ctatgctggt aggctcctgc    540
cagtgtggaa ccactgacta ctggctctca ttgacttcct tactaagcat agcaaacaga    600
ggaagaattt gttatcagta agaaaaagaa gaactatatg tgaatcctct tctttatact    660
gtaatttagt tattgatgta taaagcaact gttatgaaat aaagaaattg caataactgg    720
catataatgt ccatcagtaa atcttggtgg tggtggcaat aataaacttc tactgatagg    780
tagaatggtg tgcaagcttg tccaatcacg gattgcaggc cacatgcggc ccaggacaac    840
tttgaatgtg gcccaacaca aattcataaa ctttcataca tctcgttttt agctcatcag    900
ctatcattag cggtagtgta tttaaagtgt ggcccaagac aattcttctt attccaatgt    960
ggcccaggga aatcaaaaga ttggatgccc ctggtataga aaactaatag tgacagtgtt   1020
catatttcat gctttcccaa atacaggtat tttatttttca cattcttttt gccatgttta   1080
tataataata aagaaaaacc ctgttgattt gttggagcca ttgttatctg acagaaaata   1140
attgtttata ttttttgcac tacactgtct aaaattagca agctctcttc taatggaact   1200
gtaagaaaga tgaaatattt ttgttttatt ataaatttat ttcaccttaa ttctggtaat   1260
actcactgag tgactgtggg gtgggaaatg atctcttaag aatttgatttt ctttctattc   1320 catagtacaa actcgttctc tgttgaaaca ttcttctatc accccagtgc cctatccatg   1380
tacatgtgtt cttattgctc tagtcaaacg gtgcttataa atatctttca gaaagtttag   1440
gagaaatctg tatcctattt gacttccaat aatcatgtat tggctgtcag cttcttacct   1500
actctcagtc cagagaaata gtatttggca gccactcttt aaagtttatg ggttgtggat   1560
tgtggcggtt gatttatttt ttttatttca attgggatag aatttttttaa tatacctgta   1620 tttttgtttt gttttatgta gcttttctat taggagagt aggaaaagtg caccatttttc   1680 ttctctaaat ttccagtcca gtctttaggg gaatgttagt cttcctgaga tgggggaagg   1740
aaaatcataa tgccagtcac tttgcaaata atatttata gtgataaatg gttcattttg   1800
gttacatagg catacaagtg ggcttaaaac ttggaattta ccagggctca aaattaaaat   1860
tcttacatta gttactcgat atggatcgct tcagttgatc ttagaaaact caaggcatag   1920
```

```
atctgcaacc tcgagataac ttcgtataat gtatgctata cgaagttata tgcatggcct   1980
ccgcgccggg ttttggcgcc tcccgcgggc gccccctcc tcacggcga              2029
```

<210> SEQ ID NO 3
<211> LENGTH: 200
<212> TYPE: DNA
<213> ORGANISM: Artificial Sequence
<220> FEATURE:
<223> OTHER INFORMATION: Synthetic Oligonucleotide

<400> SEQUENCE: 3

```
cattctcagt attgttttgc caagttctaa ttccatcaga cctcgacctg cagcccctag    60
ataacttcgt ataatgtatg ctatacgaag ttatgctagc gtgatagtcc ttcacggaaa   120
gtacaagaat acacagaaaa ctgctgttta cattagtctt tcacgttttt attttattct   180
cacaaatttt aatgcaatac                                                200
```

<210> SEQ ID NO 4
<211> LENGTH: 162
<212> TYPE: PRT
<213> ORGANISM: Artificial Sequence
<220> FEATURE:
<223> OTHER INFORMATION: murine IL-15 precursor polypeptide

<400> SEQUENCE: 4

```
Met Lys Ile Leu Lys Pro Tyr Met Arg Asn Thr Ser Ile Ser Cys Tyr
 1               5                  10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser
```

<210> SEQ ID NO 5
<211> LENGTH: 162
<212> TYPE: PRT
<213> ORGANISM: Artificial Sequence
<220> FEATURE:
<223> OTHER INFORMATION: Hybrid mouse/human IL-15 precursor polypeptide

<400> SEQUENCE: 5

```
Met Lys Ile Leu Lys Pro Tyr Met Arg Asn Thr Ser Ile Ser Cys Tyr
 1               5                  10                  15

Leu Cys Phe Leu Leu Asn Ser His Phe Leu Thr Glu Ala Gly Ile His
```

```
                    20                  25                  30
Val Phe Ile Leu Gly Cys Phe Ser Ala Gly Leu Pro Lys Thr Glu Ala
                35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

```
<210> SEQ ID NO 6
<211> LENGTH: 162
<212> TYPE: PRT
<213> ORGANISM: Artificial Sequence
<220> FEATURE:
<223> OTHER INFORMATION: human IL-15 isoform 1 polypeptide

<400> SEQUENCE: 6

Met Arg Ile Ser Lys Pro His Leu Arg Ser Ile Ser Ile Gln Cys Tyr
  1               5                  10                  15

Leu Cys Leu Leu Leu Asn Ser His Phe Leu Thr Glu Ala Gly Ile His
                 20                  25                  30

Val Phe Ile Leu Gly Cys Phe Ser Ala Gly Leu Pro Lys Thr Glu Ala
                35                  40                  45

Asn Trp Val Asn Val Ile Ser Asp Leu Lys Lys Ile Glu Asp Leu Ile
     50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser
```

```
<210> SEQ ID NO 7
<211> LENGTH: 30
<212> TYPE: DNA
<213> ORGANISM: Artificial Sequence
<220> FEATURE:
<223> OTHER INFORMATION: Synthetic Oligonucleotide: hIL-15 Forward
      primer
```

```
<400> SEQUENCE: 7
gtaaraagtg atttgaaaaa aattgaagat                                    30

<210> SEQ ID NO 8
<211> LENGTH: 29
<212> TYPE: DNA
<213> ORGANISM: Artificial Sequence
<220> FEATURE:
<223> OTHER INFORMATION: Synthetic Oligonucleotide: hIL-15 Reverse
      primer

<400> SEQUENCE: 8
tacaaaactc tgcaaaaatt ctttaatat                                     29
```